US012575877B2

(12) United States Patent
Voth et al.

(10) Patent No.: US 12,575,877 B2
(45) Date of Patent: Mar. 17, 2026

(54) HIGH DENSITY ELECTRODE MAPPING CATHETER

(71) Applicant: St. Jude Medical, Cardiology Division, Inc., St. Paul, MN (US)

(72) Inventors: Eric J. Voth, Maplewood, MN (US); Gregory K. Olson, Elk River, MN (US); Brian Michael Monahan, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 948 days.

(21) Appl. No.: 17/045,377

(22) PCT Filed: Apr. 3, 2019

(86) PCT No.: PCT/US2019/025604
§ 371 (c)(1),
(2) Date: Oct. 5, 2020

(87) PCT Pub. No.: WO2019/195439
PCT Pub. Date: Oct. 10, 2019

(65) Prior Publication Data

US 2021/0153932 A1 May 27, 2021

Related U.S. Application Data

(60) Provisional application No. 62/653,031, filed on Apr. 5, 2018.

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC .................... *A61B 18/1492* (2013.01); *A61B 2018/00077* (2013.01); *A61B 2018/0016* (2013.01);
(Continued)

(58) Field of Classification Search
CPC ........ A61B 18/1492; A61B 2018/0016; A61B 2018/00214; A61B 2018/1467; A61B 2018/1497
See application file for complete search history.

(56) References Cited

U.S. PATENT DOCUMENTS

| | | | |
|---|---|---|---|
| 4,522,212 A | 6/1985 | Gelinas et al. | |
| 5,224,939 A | 7/1993 | Holman et al. | |
(Continued)

FOREIGN PATENT DOCUMENTS

| | | |
|---|---|---|
| AU | 2015202258 A1 | 5/2015 |
| AU | 2016204351 A1 | 1/2017 |
(Continued)

*Primary Examiner* — Daniel W Fowler
(74) *Attorney, Agent, or Firm* — Kilpatrick Townsend & Stockton LLP

(57) ABSTRACT

A medical device can comprise a catheter shaft comprising a proximal end and a distal end, the catheter shaft defining a catheter shaft longitudinal axis. A flexible tip portion can be located adjacent to the distal end of the catheter shaft, the flexible tip portion comprising a flexible framework. A plurality of curved microelectrodes can be disposed on the flexible framework and can form a flexible array of curved microelectrodes adapted to conform to tissue.

9 Claims, 14 Drawing Sheets

(52) U.S. Cl.
CPC .............. *A61B 2018/00839* (2013.01); *A61B 2018/1467* (2013.01)

(56) References Cited

U.S. PATENT DOCUMENTS

| | | | |
|---|---|---|---|
| 5,380,301 A | 1/1995 | Prichard et al. | |
| 5,400,783 A | 3/1995 | Pomeranz et al. | |
| 5,456,254 A | 10/1995 | Pietroski et al. | |
| 5,626,136 A | 5/1997 | Webster, Jr. | |
| 5,702,438 A | 12/1997 | Avitall | |
| 5,715,817 A | 2/1998 | Stevens-Wright et al. | |
| 5,715,832 A | 2/1998 | Koblish et al. | |
| 5,788,692 A | 8/1998 | Campbell et al. | |
| 5,827,278 A | 10/1998 | Webster, Jr. | |
| 5,876,373 A | 3/1999 | Giba et al. | |
| 5,964,757 A | 10/1999 | Ponzi | |
| 6,029,091 A | 2/2000 | de la Rama et al. | |
| 6,071,282 A | 6/2000 | Fleischman | |
| 6,074,379 A | 6/2000 | Prichard | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,267,746 B1 | 7/2001 | Bumbalough | |
| 6,273,404 B1 | 8/2001 | Holman et al. | |
| 6,415,187 B1 | 7/2002 | Kuzma et al. | |
| 6,491,681 B1 | 12/2002 | Kunis et al. | |
| 6,522,932 B1 | 2/2003 | Kuzma et al. | |
| 6,554,794 B1 | 4/2003 | Mueller et al. | |
| 6,652,515 B1 | 11/2003 | Maguire et al. | |
| 6,658,302 B1 | 12/2003 | Kuzma et al. | |
| 6,961,602 B2 | 11/2005 | Fuimaono et al. | |
| 7,004,937 B2 | 2/2006 | Lentz et al. | |
| 7,027,851 B2 | 4/2006 | Mejia | |
| 7,089,045 B2 | 8/2006 | Fuimaono et al. | |
| 7,099,712 B2 | 8/2006 | Fuimaono et al. | |
| 7,214,220 B2 | 5/2007 | McGlinch et al. | |
| 7,217,256 B2 | 5/2007 | Di Palma | |
| 7,228,164 B2 | 6/2007 | Fuimaono et al. | |
| 7,257,435 B2 | 8/2007 | Plaza | |
| 7,412,274 B2 | 8/2008 | Mejia | |
| 7,429,261 B2 | 9/2008 | Kunis et al. | |
| 7,561,907 B2 | 7/2009 | Fuimaono et al. | |
| 7,608,063 B2 | 10/2009 | Le et al. | |
| 7,625,365 B2 | 12/2009 | McGlinch et al. | |
| 7,666,204 B2 | 2/2010 | Thornton et al. | |
| 7,959,601 B2 | 6/2011 | McDaniel et al. | |
| 7,985,215 B2 | 7/2011 | Guo et al. | |
| 8,103,327 B2 | 1/2012 | Harlev et al. | |
| 8,137,321 B2 | 3/2012 | Argentine | |
| 8,157,848 B2 | 4/2012 | Zhang et al. | |
| 8,221,390 B2 | 7/2012 | Pal et al. | |
| 8,271,099 B1 | 9/2012 | Swanson | |
| 8,273,016 B2 | 9/2012 | O'Sullivan | |
| 8,376,990 B2 | 2/2013 | Ponzi et al. | |
| 8,391,947 B2 | 3/2013 | Urman et al. | |
| 8,447,377 B2 | 5/2013 | Harlev et al. | |
| 8,486,063 B2 | 7/2013 | Werneth et al. | |
| 8,565,894 B2 | 10/2013 | Vetter et al. | |
| 8,603,069 B2 | 12/2013 | Selkee | |
| 8,608,703 B2 | 12/2013 | Riles et al. | |
| 8,649,880 B1 | 2/2014 | Parker, Jr. | |
| 8,700,120 B2 | 4/2014 | Koblish | |
| 8,706,193 B2 | 4/2014 | Govari et al. | |
| 8,744,599 B2 | 6/2014 | Tegg | |
| 8,755,861 B2 | 6/2014 | Harlev et al. | |
| 8,771,267 B2 | 7/2014 | Kunis et al. | |
| 8,777,929 B2 | 7/2014 | Schneider et al. | |
| 8,792,962 B2 | 7/2014 | Esguerra et al. | |
| 8,814,824 B2 | 8/2014 | Kauphusman et al. | |
| 8,814,825 B2 | 8/2014 | Tegg et al. | |
| 8,882,705 B2 | 11/2014 | McDaniel et al. | |
| 8,894,610 B2 | 11/2014 | Macnamara et al. | |
| 8,979,841 B2 | 3/2015 | Kunis et al. | |
| 8,996,091 B2 | 3/2015 | de la Rama et al. | |
| 9,017,308 B2 | 4/2015 | Klisch et al. | |
| 9,033,917 B2 | 5/2015 | Magana et al. | |
| 9,044,245 B2 | 6/2015 | Condie et al. | |
| 9,050,010 B2 | 6/2015 | Bui et al. | |
| 9,101,733 B2 | 8/2015 | McDaniel | |
| 9,204,929 B2 | 12/2015 | Solis | |
| 9,216,056 B2 | 12/2015 | Datta et al. | |
| 9,247,990 B2 | 2/2016 | Kauphusman et al. | |
| 9,326,815 B2 | 5/2016 | Watson | |
| 9,339,631 B2 | 5/2016 | Graham et al. | |
| 9,433,751 B2 | 9/2016 | Ponzi et al. | |
| 9,433,752 B2 | 9/2016 | Jimenez et al. | |
| 9,468,495 B2 | 10/2016 | Kunis et al. | |
| 9,474,486 B2 | 10/2016 | Eliason et al. | |
| 9,486,280 B2 | 11/2016 | Koblish et al. | |
| 9,486,282 B2 | 11/2016 | Solis | |
| 9,522,035 B2 | 12/2016 | Highsmith | |
| 9,532,703 B2 | 1/2017 | Huszar et al. | |
| 9,539,413 B2 | 1/2017 | Ogle | |
| 9,629,675 B2 | 4/2017 | Kleshinski et al. | |
| 9,649,158 B2 | 5/2017 | Datta et al. | |
| 9,687,166 B2 | 6/2017 | Subramaniam et al. | |
| 9,693,733 B2 | 7/2017 | Altmann et al. | |
| 9,694,159 B2 | 7/2017 | Schneider et al. | |
| 9,694,161 B2 | 7/2017 | Selkee | |
| 9,713,418 B2 | 7/2017 | Huszar et al. | |
| 9,788,895 B2 | 10/2017 | Solis | |
| 9,808,171 B2 | 11/2017 | Balachandran et al. | |
| 9,820,664 B2 | 11/2017 | Hoitink et al. | |
| 9,833,608 B2 | 12/2017 | Masson | |
| 9,844,645 B2 | 12/2017 | Pai et al. | |
| 9,848,795 B2 | 12/2017 | Marecki et al. | |
| 9,907,480 B2 | 3/2018 | Basu et al. | |
| 9,919,132 B2 | 3/2018 | Tegg et al. | |
| 9,949,656 B2 | 4/2018 | Wu et al. | |
| 9,986,949 B2 | 6/2018 | Govari et al. | |
| 10,004,877 B2 | 6/2018 | Tegg | |
| 10,034,637 B2 | 7/2018 | Harlev et al. | |
| 10,052,457 B2 | 8/2018 | Nguyen et al. | |
| 10,065,019 B2 | 9/2018 | Hamuro et al. | |
| 10,099,036 B2 | 10/2018 | Heideman et al. | |
| 10,118,022 B2 | 11/2018 | Helgeson et al. | |
| 10,130,423 B1 | 11/2018 | Viswanathan et al. | |
| 10,136,829 B2 | 11/2018 | Deno et al. | |
| 10,143,394 B2 | 12/2018 | Solis | |
| 10,172,673 B2 | 1/2019 | Viswanathan et al. | |
| 10,285,610 B2 | 5/2019 | Wu | |
| 10,322,261 B2 | 6/2019 | Pai et al. | |
| 10,362,952 B2 | 7/2019 | Basu et al. | |
| 10,362,954 B2 | 7/2019 | de la Rama et al. | |
| 10,376,170 B2 | 8/2019 | Quinn et al. | |
| 10,384,036 B2 | 8/2019 | Romoscanu | |
| 10,398,500 B2 | 9/2019 | Huszar et al. | |
| 10,470,682 B2 | 11/2019 | Deno et al. | |
| 10,478,247 B2 | 11/2019 | Litscher et al. | |
| 10,478,325 B2 | 11/2019 | Syed | |
| 10,492,729 B2 | 12/2019 | de la Rama et al. | |
| 10,506,938 B2 | 12/2019 | Wu et al. | |
| 10,537,259 B2 | 1/2020 | Wu et al. | |
| 10,542,899 B2 | 1/2020 | Wu et al. | |
| 10,556,091 B2 | 2/2020 | Truhler et al. | |
| 10,575,742 B2 | 3/2020 | Wu et al. | |
| 10,575,745 B2 | 3/2020 | Solis | |
| 10,578,737 B2 | 3/2020 | Gliner et al. | |
| 10,595,738 B2 * | 3/2020 | Sterrett .................. A61B 18/14 |
| 10,595,740 B2 | 3/2020 | Hoitink et al. | |
| 10,602,948 B2 | 3/2020 | Wu et al. | |
| 10,646,692 B2 | 5/2020 | Tegg et al. | |
| 10,653,423 B2 | 5/2020 | Starnes | |
| 10,702,177 B2 | 7/2020 | Aujla | |
| 10,702,677 B2 | 7/2020 | Okamura et al. | |
| 10,737,060 B2 | 8/2020 | Gupta et al. | |
| 10,813,590 B2 | 10/2020 | Ruppersberg | |
| 10,835,712 B2 | 11/2020 | Wada | |
| 10,842,990 B2 | 11/2020 | de la Rama et al. | |
| 10,857,349 B2 | 12/2020 | de la Rama et al. | |
| 10,869,992 B2 | 12/2020 | Pai et al. | |
| 10,898,685 B2 | 1/2021 | Tegg | |

(56) References Cited

U.S. PATENT DOCUMENTS

| | | |
|---|---|---|
| 10,905,347 B2 | 2/2021 | Fuentes-ortega et al. |
| 10,912,925 B2 | 2/2021 | Houck |
| 10,932,685 B2 | 3/2021 | Wu |
| 10,945,626 B2 | 3/2021 | Fuentes-Ortega et al. |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,973,427 B2 | 4/2021 | Aujla |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,123,051 B2 | 9/2021 | Van Der Linde et al. |
| 11,141,568 B2 | 10/2021 | Hsueh et al. |
| 11,160,482 B2 | 11/2021 | Solis |
| 11,172,858 B2 | 11/2021 | Olson et al. |
| D940,310 S | 1/2022 | de la Rama et al. |
| 11,272,886 B2 | 3/2022 | Harlev et al. |
| D951,438 S | 5/2022 | de la Rama et al. |
| D952,140 S | 5/2022 | de la Rama et al. |
| D952,843 S | 5/2022 | de la Rama et al. |
| 11,382,690 B2 | 7/2022 | Smith et al. |
| 11,382,743 B2 | 7/2022 | Marchand et al. |
| 11,383,078 B2 | 7/2022 | de la Rama et al. |
| 11,419,673 B2 | 8/2022 | Kauphusman et al. |
| 11,426,111 B2 | 8/2022 | Olson |
| 11,433,220 B2 | 9/2022 | Oliverius et al. |
| 11,439,460 B2 | 9/2022 | Sliwa et al. |
| 11,446,471 B2 | 9/2022 | Grunewald |
| D966,506 S | 10/2022 | de la Rama et al. |
| D966,507 S | 10/2022 | de la Rama et al. |
| 11,478,299 B2 | 10/2022 | Webster et al. |
| 11,484,690 B2 | 11/2022 | Tegg et al. |
| 11,491,311 B2 | 11/2022 | Selkee |
| 11,504,205 B2 | 11/2022 | Brucker et al. |
| 11,511,078 B2 | 11/2022 | Gonzalez |
| 11,517,715 B2 | 12/2022 | Govari |
| 11,523,748 B2 | 12/2022 | Esguerra Wilczynski et al. |
| 11,540,876 B2 | 1/2023 | Oliverius et al. |
| 11,547,437 B2 | 1/2023 | Zarembinski |
| 11,583,334 B2 | 2/2023 | Caples et al. |
| 11,602,630 B2 | 3/2023 | Vetter et al. |
| 11,617,616 B2 | 4/2023 | Clark et al. |
| 11,617,859 B2 | 4/2023 | Hsueh et al. |
| 11,617,861 B2 | 4/2023 | Pai et al. |
| 11,622,806 B2 | 4/2023 | Romoscanu |
| 11,628,009 B2 | 4/2023 | Aujla |
| 11,660,119 B2 | 5/2023 | Hassett |
| 11,672,947 B2 | 6/2023 | Tegg et al. |
| 11,690,552 B2 | 7/2023 | Wu et al. |
| 11,723,574 B2 | 8/2023 | Wu et al. |
| 11,786,301 B2 | 10/2023 | Olson |
| 11,806,152 B2 | 11/2023 | Zeidan et al. |
| 11,813,410 B2 | 11/2023 | Olson et al. |
| 11,857,250 B2 | 1/2024 | Corvi et al. |
| 11,938,316 B2 | 3/2024 | Feler et al. |
| 11,950,897 B2 | 4/2024 | Esguerra Wilczynski et al. |
| 11,957,847 B2 | 4/2024 | Houck |
| 11,992,321 B2 | 5/2024 | Solis |
| 12,004,805 B2 | 6/2024 | Schuler et al. |
| 12,011,216 B2 | 6/2024 | Zirkle et al. |
| 12,036,027 B2 | 7/2024 | Olson et al. |
| 12,036,371 B2 | 7/2024 | Hsueh et al. |
| 12,064,168 B2 | 8/2024 | Harlev et al. |
| 12,076,079 B2 | 9/2024 | Oliverius et al. |
| 12,089,940 B2 | 9/2024 | Hoitink et al. |
| 12,097,034 B2 | 9/2024 | Wu et al. |
| 12,109,031 B2 | 10/2024 | Deno et al. |
| 12,114,922 B2 | 10/2024 | Harlev et al. |
| 12,121,357 B2 | 10/2024 | de la Rama et al. |
| 12,121,438 B2 | 10/2024 | Dehdashtian et al. |
| 12,144,629 B2 | 11/2024 | Wu et al. |
| 12,193,823 B2 | 1/2025 | Wu et al. |
| 12,214,206 B2 | 2/2025 | Ward et al. |
| 12,232,908 B2 | 2/2025 | Stigall et al. |
| 12,246,143 B2 | 3/2025 | Leeflang et al. |
| 12,256,913 B2 | 3/2025 | Nunan |
| 12,256,984 B2 | 3/2025 | Ku et al. |
| 12,263,338 B2 | 4/2025 | de la Rama et al. |
| 12,324,620 B2 | 6/2025 | de la Rama et al. |
| 12,337,124 B2 | 6/2025 | Campbell et al. |
| 2002/0095202 A1 | 7/2002 | Schmidt |
| 2002/0165484 A1 | 11/2002 | Bowe et al. |
| 2005/0159741 A1 | 7/2005 | Paul et al. |
| 2007/0156128 A1* | 7/2007 | Jimenez ............. A61B 18/1492 |
| | | 606/41 |
| 2009/0198300 A1 | 8/2009 | Zhang et al. |
| 2011/0118726 A1 | 5/2011 | de la Rama et al. |
| 2012/0265198 A1* | 10/2012 | Crow ................. A61B 18/1492 |
| | | 606/41 |
| 2012/0271302 A1 | 10/2012 | Behl et al. |
| 2012/0296232 A1 | 11/2012 | Ng |
| 2013/0172715 A1* | 7/2013 | Just ...................... A61B 5/6858 |
| | | 606/41 |
| 2013/0253504 A1 | 9/2013 | Fang |
| 2013/0274582 A1 | 10/2013 | Afonso et al. |
| 2014/0088585 A1* | 3/2014 | Hill ........................ A61B 18/18 |
| | | 606/33 |
| 2014/0100639 A1 | 4/2014 | Lee et al. |
| 2014/0200639 A1 | 7/2014 | de la Rama |
| 2014/0228838 A1* | 8/2014 | Kirschenman ......... A61N 1/056 |
| | | 606/41 |
| 2014/0269602 A1 | 9/2014 | Kawagishi |
| 2014/0296846 A1 | 10/2014 | Huszar et al. |
| 2014/0296849 A1 | 10/2014 | Coe et al. |
| 2014/0296902 A1 | 10/2014 | Huszar et al. |
| 2014/0316496 A1 | 10/2014 | Masson et al. |
| 2014/0336636 A1 | 11/2014 | Huszar et al. |
| 2014/0350564 A1 | 11/2014 | Huszar et al. |
| 2015/0001191 A1 | 1/2015 | Lee et al. |
| 2015/0005764 A1* | 1/2015 | Hanson .............. A61B 18/1492 |
| | | 606/41 |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0351652 A1* | 12/2015 | Marecki ............. A61B 18/1492 |
| | | 29/829 |
| 2016/0143588 A1* | 5/2016 | Hoitink ................ A61B 5/6859 |
| | | 600/374 |
| 2016/0213423 A1 | 7/2016 | Kauphusman et al. |
| 2016/0213916 A1 | 7/2016 | de la Rama |
| 2016/0278851 A1 | 9/2016 | Mannion et al. |
| 2016/0317094 A1 | 11/2016 | Byrd et al. |
| 2016/0331471 A1 | 11/2016 | Deno et al. |
| 2016/0331933 A1 | 11/2016 | Knutsen |
| 2016/0374582 A1 | 12/2016 | Wu et al. |
| 2016/0374753 A1* | 12/2016 | Wu ................... A61B 18/1492 |
| | | 606/41 |
| 2017/0000365 A1 | 1/2017 | Wu et al. |
| 2017/0035497 A1* | 2/2017 | Nagale .............. A61B 18/1492 |
| 2017/0042449 A1 | 2/2017 | Deno et al. |
| 2017/0049348 A1 | 2/2017 | Deno et al. |
| 2017/0071661 A1* | 3/2017 | Hoitink ................. A61B 5/287 |
| 2017/0112404 A1 | 4/2017 | de la Rama et al. |
| 2017/0112405 A1 | 4/2017 | Sterrett et al. |
| 2017/0273738 A1 | 9/2017 | Wu |
| 2017/0281193 A1* | 10/2017 | Asirvatham ..... A61B 17/12177 |
| 2017/0319269 A1 | 11/2017 | Oliverius et al. |
| 2017/0367756 A1 | 12/2017 | Sliwa et al. |
| 2018/0042506 A1 | 2/2018 | Locke et al. |
| 2018/0042667 A1 | 2/2018 | Pappone et al. |
| 2018/0056038 A1 | 3/2018 | Aujla |
| 2018/0070845 A1 | 3/2018 | Hoitink et al. |
| 2018/0085064 A1 | 3/2018 | Auerbach et al. |
| 2018/0085160 A1* | 3/2018 | Viswanathan ......... A61N 1/371 |
| 2018/0116539 A1 | 5/2018 | Olson et al. |
| 2018/0161093 A1 | 6/2018 | Basu et al. |

(56) References Cited

U.S. PATENT DOCUMENTS

| | | |
|---|---|---|
| 2018/0193089 A1 | 7/2018 | Wu |
| 2018/0229030 A1 | 8/2018 | Dubuclet et al. |
| 2018/0235496 A1 | 8/2018 | Wu et al. |
| 2018/0303361 A1 | 10/2018 | Wu et al. |
| 2018/0335519 A1 | 11/2018 | Gliner et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0175043 A1 | 6/2019 | Wu et al. |
| 2019/0192826 A1 | 6/2019 | Wada |
| 2019/0239812 A1 | 8/2019 | Botzer et al. |
| 2020/0000359 A1 | 1/2020 | de la Rama et al. |
| 2020/0054391 A1 | 2/2020 | Litscher et al. |
| 2020/0069365 A1 | 3/2020 | Harlev et al. |
| 2020/0077912 A1 | 3/2020 | Wu et al. |
| 2020/0121894 A1 | 4/2020 | Prabhu et al. |
| 2020/0138378 A1 | 5/2020 | de la Rama et al. |
| 2020/0155021 A1 | 5/2020 | Wu et al. |
| 2020/0214635 A1 | 7/2020 | Dahlen et al. |
| 2020/0221966 A1 | 7/2020 | Wu et al. |
| 2020/0229727 A1 | 7/2020 | Hoitink et al. |
| 2020/0229866 A1 | 7/2020 | Harlev et al. |
| 2020/0253496 A1 | 8/2020 | Deno et al. |
| 2020/0329989 A1 | 10/2020 | Aujla |
| 2020/0405166 A1 | 12/2020 | Wu et al. |
| 2021/0068693 A1 | 3/2021 | Fuentes-ortega et al. |
| 2021/0145342 A1 | 5/2021 | Wang |
| 2021/0187246 A1 | 6/2021 | Houck |
| 2021/0204871 A1 | 7/2021 | Goedeke et al. |
| 2021/0228136 A1 | 7/2021 | Fuentes-ortega et al. |
| 2021/0228137 A1 | 7/2021 | Aujla |
| 2021/0267693 A1 | 9/2021 | Deno et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |
| 2022/0273913 A1 | 9/2022 | Worley et al. |
| 2022/0354568 A1 | 11/2022 | Pappone et al. |
| 2022/0370792 A1 | 11/2022 | de la Rama et al. |
| 2022/0387012 A1 | 12/2022 | Nunan |
| 2022/0401693 A1 | 12/2022 | Oliverius et al. |
| 2023/0000415 A1 | 1/2023 | Olson |
| 2023/0011509 A1 | 1/2023 | Sterrett et al. |
| 2023/0078216 A1 | 3/2023 | Govari |
| 2023/0084626 A1 | 3/2023 | Grunewald |
| 2023/0114222 A1 | 4/2023 | Esguerra Wilczynski et al. |
| 2023/0121397 A1 | 4/2023 | Oliverius et al. |
| 2023/0172661 A1 | 6/2023 | Harlev et al. |
| 2023/0190369 A1 | 6/2023 | Caples et al. |
| 2023/0284956 A1 | 9/2023 | Wu et al. |
| 2023/0329618 A1 | 10/2023 | Wu et al. |
| 2023/0329784 A1 | 10/2023 | Stewart et al. |
| 2023/0404657 A1 | 12/2023 | Olson |
| 2024/0033470 A1 | 2/2024 | Olson et al. |
| 2024/0081905 A1 | 3/2024 | Corvi et al. |
| 2024/0173070 A1 | 5/2024 | Selkee et al. |
| 2024/0198054 A1 | 6/2024 | Schultz |
| 2024/0252815 A1 | 8/2024 | de la Rama et al. |
| 2024/0277277 A1 | 8/2024 | Hoitink et al. |
| 2024/0325691 A1 | 10/2024 | Bogusky |
| 2024/0350063 A1 | 10/2024 | Olson et al. |
| 2024/0366299 A1 | 11/2024 | Dando et al. |
| 2024/0415438 A1 | 12/2024 | Wu et al. |
| 2025/0009272 A1 | 1/2025 | de la Rama et al. |
| 2025/0025231 A1 | 1/2025 | Oliverius et al. |
| 2025/0032028 A1 | 1/2025 | Deno et al. |
| 2025/0032181 A1 | 1/2025 | Harlev et al. |
| 2025/0040853 A1 | 2/2025 | Wu et al. |
| 2025/0049460 A1 | 2/2025 | Worrell et al. |
| 2025/0072897 A1 | 3/2025 | Reu et al. |
| 2025/0082903 A1 | 3/2025 | Hsueh et al. |
| 2025/0090070 A1 | 3/2025 | Wu et al. |
| 2025/0090807 A1 | 3/2025 | Padilla et al. |
| 2025/0152932 A1 | 5/2025 | de la Rama et al. |
| 2025/0160942 A1 | 5/2025 | Ku et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 101927053 B | 1/2015 |
| CN | 103157168 B | 4/2015 |
| CN | 105960201 A | 9/2016 |
| CN | 106859765 A | 6/2017 |
| CN | 106901831 A | 6/2017 |
| CN | 107405099 A | 11/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 105960200 B | 8/2019 |
| CN | 105451680 B | 10/2019 |
| CN | 110536646 A | 12/2019 |
| CN | 105960201 B | 3/2020 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| CN | 111246907 B | 7/2022 |
| CN | 107773300 B | 8/2022 |
| CN | 108567424 B | 8/2022 |
| CN | 106859638 B | 10/2022 |
| CN | 108283520 B | 10/2022 |
| CN | 110547865 B | 10/2022 |
| CN | 107343816 B | 11/2022 |
| CN | 115281680 A | 11/2022 |
| CN | 115444549 A | 12/2022 |
| CN | 107343784 B | 2/2023 |
| CN | 110520067 B | 5/2023 |
| CN | 111225627 B | 5/2023 |
| CN | 116158839 A | 5/2023 |
| CN | 106419897 B | 6/2023 |
| CN | 111065350 B | 6/2023 |
| CN | 109259854 B | 10/2023 |
| CN | 111657866 B | 10/2023 |
| CN | 111836579 B | 3/2024 |
| CN | 112704546 B | 3/2024 |
| CN | 117942483 A | 4/2024 |
| CN | 117958829 A | 5/2024 |
| CN | 118384409 A | 7/2024 |
| CN | 111683581 B | 9/2024 |
| CN | 111683614 B | 10/2024 |
| CN | 111918606 B | 1/2025 |
| CN | 112040860 B | 5/2025 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |

(56) References Cited

FOREIGN PATENT DOCUMENTS

| | | | |
|---|---|---|---|
| EP | 2732843 | A1 | 5/2014 |
| EP | 2747680 | A2 | 7/2014 |
| EP | 2752153 | A1 | 7/2014 |
| EP | 2907462 | A1 | 8/2015 |
| EP | 2915555 | A1 | 9/2015 |
| EP | 1968679 | B1 | 9/2016 |
| EP | 2241279 | B1 | 9/2016 |
| EP | 3111871 | A1 | 1/2017 |
| EP | 3111872 | A1 | 1/2017 |
| EP | 2796103 | B1 | 2/2017 |
| EP | 3222209 | A1 | 9/2017 |
| EP | 2792322 | B1 | 10/2017 |
| EP | 2792323 | B1 | 10/2017 |
| EP | 3115076 | A4 | 10/2017 |
| EP | 3117863 | A4 | 10/2017 |
| EP | 3030182 | B1 | 1/2018 |
| EP | 3287092 | A1 | 2/2018 |
| EP | 3111871 | B1 | 3/2018 |
| EP | 3111872 | B1 | 4/2018 |
| EP | 3057488 | B1 | 5/2018 |
| EP | 2848226 | B1 | 7/2018 |
| EP | 3345540 | A1 | 7/2018 |
| EP | 3363397 | A1 | 8/2018 |
| EP | 3391928 | A1 | 10/2018 |
| EP | 3122276 | B1 | 11/2018 |
| EP | 3398549 | A1 | 11/2018 |
| EP | 3403571 | A1 | 11/2018 |
| EP | 1759668 | B1 | 12/2018 |
| EP | 3020352 | B1 | 12/2018 |
| EP | 3037122 | B1 | 12/2018 |
| EP | 2234537 | B1 | 1/2019 |
| EP | 2569040 | B1 | 2/2019 |
| EP | 3023052 | B1 | 3/2019 |
| EP | 3073908 | B1 | 4/2019 |
| EP | 3466363 | A1 | 4/2019 |
| EP | 2550989 | B1 | 6/2019 |
| EP | 3512589 | A1 | 7/2019 |
| EP | 3512590 | A1 | 7/2019 |
| EP | 3527125 | A1 | 8/2019 |
| EP | 3531903 | A1 | 9/2019 |
| EP | 3434218 | B1 | 2/2020 |
| EP | 2908723 | B1 | 3/2020 |
| EP | 3335658 | B1 | 4/2020 |
| EP | 3073907 | B1 | 6/2020 |
| EP | 3114987 | B1 | 8/2020 |
| EP | 3178516 | B1 | 9/2020 |
| EP | 3708104 | A1 | 9/2020 |
| EP | 3711662 | A1 | 9/2020 |
| EP | 3721796 | A1 | 10/2020 |
| EP | 3738508 | A1 | 11/2020 |
| EP | 3738509 | A1 | 11/2020 |
| EP | 3340916 | B1 | 12/2020 |
| EP | 3579908 | B1 | 12/2020 |
| EP | 3749174 | A1 | 12/2020 |
| EP | 3749191 | A1 | 12/2020 |
| EP | 3749192 | A1 | 12/2020 |
| EP | 3750475 | A1 | 12/2020 |
| EP | 2155301 | B1 | 4/2021 |
| EP | 3432820 | B1 | 4/2021 |
| EP | 3476331 | B1 | 5/2021 |
| EP | 3579758 | B1 | 5/2021 |
| EP | 2809254 | B1 | 6/2021 |
| EP | 3508245 | B1 | 7/2021 |
| EP | 3858277 | A1 | 8/2021 |
| EP | 3892221 | A1 | 10/2021 |
| EP | 3932343 | A4 | 1/2022 |
| EP | 3791820 | B9 | 4/2022 |
| EP | 4000506 | A1 | 5/2022 |
| EP | 4039215 | A1 | 8/2022 |
| EP | 4041112 | A1 | 8/2022 |
| EP | 3363397 | B1 | 9/2022 |
| EP | 3609414 | B1 | 11/2022 |
| EP | 4101372 | A1 | 12/2022 |
| EP | 2844193 | B1 | 1/2023 |
| EP | 3100696 | B1 | 1/2023 |
| EP | 3166524 | B1 | 1/2023 |
| EP | 4115936 | A1 | 1/2023 |
| EP | 4134032 | A1 | 2/2023 |
| EP | 3115076 | B1 | 3/2023 |
| EP | 3658054 | B1 | 3/2023 |
| EP | 4179991 | A1 | 5/2023 |
| EP | 2803329 | B1 | 6/2023 |
| EP | 3015064 | B1 | 6/2023 |
| EP | 3141183 | B1 | 6/2023 |
| EP | 3398549 | B1 | 6/2023 |
| EP | 4190232 | A1 | 6/2023 |
| EP | 2816966 | B1 | 10/2023 |
| EP | 3113671 | B1 | 10/2023 |
| EP | 3681427 | B1 | 10/2023 |
| EP | 3738509 | B1 | 10/2023 |
| EP | 3209234 | B1 | 11/2023 |
| EP | 3527125 | B1 | 11/2023 |
| EP | 3721796 | B1 | 11/2023 |
| EP | 3731747 | B1 | 11/2023 |
| EP | 4233699 | A3 | 11/2023 |
| EP | 4272631 | A2 | 11/2023 |
| EP | 3192442 | B1 | 1/2024 |
| EP | 3892221 | B1 | 1/2024 |
| EP | 4298995 | A2 | 1/2024 |
| EP | 3738508 | B1 | 2/2024 |
| EP | 3124069 | B1 | 4/2024 |
| EP | 4360572 | A1 | 5/2024 |
| EP | 4364765 | A2 | 5/2024 |
| EP | 3498156 | B1 | 6/2024 |
| EP | 4344722 | A3 | 6/2024 |
| EP | 3573559 | B1 | 7/2024 |
| EP | 4272631 | A3 | 7/2024 |
| EP | 4205685 | B1 | 8/2024 |
| EP | 4417112 | A2 | 8/2024 |
| EP | 3629964 | B1 | 9/2024 |
| EP | 3184035 | B1 | 10/2024 |
| EP | 4101372 | B1 | 12/2024 |
| EP | 3737453 | B1 | 1/2025 |
| EP | 2915555 | B1 | 2/2025 |
| IL | 246415 | B | 12/2019 |
| IN | 201614021431 | A | 12/2016 |
| IN | 201614021432 | A | 12/2016 |
| IN | 201614021450 | A | 12/2016 |
| JP | 2010507403 | A | 3/2010 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 2013510689 | A | 3/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 2014512226 | A | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 6059737 | B2 | 12/2016 |
| JP | 2017012750 | A | 1/2017 |
| JP | 2017012755 | A | 1/2017 |
| JP | 2017038919 | A | 2/2017 |
| JP | 2017051211 | A | 3/2017 |
| JP | 2017104552 | A | 6/2017 |
| JP | 6246742 | B2 | 12/2017 |
| JP | 6342524 | B2 | 6/2018 |
| JP | 6434495 | B2 | 12/2018 |
| JP | 6445509 | B2 | 12/2018 |
| JP | 6445742 | B1 | 12/2018 |
| JP | 6466114 | B2 | 2/2019 |
| JP | 6479005 | B2 | 2/2019 |
| JP | 6515084 | B2 | 5/2019 |
| JP | 6528010 | B1 | 6/2019 |
| JP | 6655655 | B2 | 2/2020 |
| JP | 6746734 | B2 | 8/2020 |
| JP | 6776021 | B2 | 10/2020 |

(56) References Cited

FOREIGN PATENT DOCUMENTS

| | | | |
|---|---|---|---|
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 2021501011 | A | 1/2021 |
| JP | 6843502 | B2 | 3/2021 |
| JP | 6894004 | B2 | 6/2021 |
| JP | 6920312 | B2 | 8/2021 |
| JP | 6926306 | B2 | 8/2021 |
| JP | 6932484 | B2 | 8/2021 |
| JP | 6936872 | B2 | 9/2021 |
| JP | 6980386 | B2 | 11/2021 |
| JP | 2022020838 | A | 2/2022 |
| JP | 7102558 | B2 | 7/2022 |
| JP | 7106301 | B2 | 7/2022 |
| JP | 2023002720 | A | 1/2023 |
| JP | 7220242 | B2 | 2/2023 |
| JP | 7230168 | B2 | 2/2023 |
| JP | 7242665 | B2 | 3/2023 |
| JP | 7242816 | B2 | 3/2023 |
| JP | 7246319 | B2 | 3/2023 |
| JP | 2023027202 | A | 3/2023 |
| JP | 2023033335 | A | 3/2023 |
| JP | 7262919 | B2 | 4/2023 |
| JP | 7275333 | B2 | 5/2023 |
| JP | 7282759 | B2 | 5/2023 |
| JP | 7292822 | B2 | 6/2023 |
| JP | 7394766 | B2 | 11/2023 |
| JP | 7400050 | B2 | 12/2023 |
| JP | 7423550 | B2 | 1/2024 |
| JP | 2024012693 | A | 1/2024 |
| JP | 7465944 | B2 | 4/2024 |
| JP | 2024059810 | A | 5/2024 |
| JP | 7514764 | B2 | 7/2024 |
| JP | 7530317 | B2 | 8/2024 |
| JP | 2024103761 | A | 8/2024 |
| JP | 2024156696 | A | 11/2024 |
| JP | 7628563 | B2 | 2/2025 |
| JP | 2025026734 | A | 2/2025 |
| JP | 2025026852 | A | 2/2025 |
| JP | 2025027101 | A | 2/2025 |
| JP | 7641330 | B2 | 3/2025 |
| JP | 7646980 | B2 | 4/2025 |
| RU | 2016124794 | A | 12/2017 |
| RU | 2016124801 | A | 12/2017 |
| RU | 2016125763 | A | 1/2018 |
| WO | 9843530 | A1 | 10/1998 |
| WO | 0168178 | A1 | 9/2001 |
| WO | 2008091197 | A1 | 7/2008 |
| WO | 2012/145077 | A1 | 10/2012 |
| WO | 2014/113612 | A1 | 7/2014 |
| WO | 2015057521 | A1 | 4/2015 |
| WO | 2015095577 | A1 | 6/2015 |
| WO | 2015130824 | A1 | 9/2015 |
| WO | 2016001015 | A1 | 1/2016 |
| WO | 2016/090175 | A1 | 6/2016 |
| WO | 2017/070559 | A1 | 4/2017 |
| WO | 2017070531 | A1 | 4/2017 |
| WO | 2017098198 | A1 | 6/2017 |
| WO | 2018053148 | A1 | 3/2018 |
| WO | 2018053164 | A1 | 3/2018 |
| WO | 2018136741 | A1 | 7/2018 |

* cited by examiner

HIGH DENSITY ELECTRODE MAPPING CATHETER

CROSS-REFERENCE TO RELATED APPLICATIONS

This application is the national stage of international application no. PCT/US2019/025604, filed 3 Apr. 2019 (the '604 application), and published under International publication no. WO 2019/195439 on 10 Oct. 2019. This application claims priority to U.S. provisional application No. 62/653,031, filed 5 Apr. 2018 (the '031 application). The '604 application and the '031 application are both hereby incorporated by reference in their entirety as though fully set forth herein.

A. FIELD OF THE DISCLOSURE

This disclosure relates to a high density electrode mapping catheter.

B. BACKGROUND ART

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments herein provide a medical device that comprises a catheter shaft comprising a proximal end and a distal end, the catheter shaft defining a catheter shaft longitudinal axis. A flexible tip portion can be located adjacent to the distal end of the catheter shaft, the flexible tip portion comprising a flexible framework. A plurality of curved microelectrodes can be disposed on the flexible framework and can form a flexible array of curved microelectrodes adapted to conform to tissue.

Various embodiments herein provide a medical device that comprises a catheter shaft that includes a proximal end and a distal end, the catheter shaft defining a catheter shaft longitudinal axis. A flexible tip portion can be located adjacent to the distal end of the catheter shaft, the flexible tip portion comprising a flexible framework. The flexible framework can include a first inboard arm, second inboard arm, first outboard arm, and second outboard arm, wherein the flexible framework further includes a top portion and a bottom portion. In some embodiments, a first plurality of curved electrodes can be disposed on the top portion of the flexible framework. In some embodiments, a second plurality of curved electrodes can be disposed on the bottom portion of the flexible framework.

Various embodiments herein provide a medical device that comprises a catheter. The catheter shaft can comprise a proximal end and a distal end. The catheter shaft can define a catheter shaft longitudinal axis. A flexible tip portion can be located adjacent to the distal end of the catheter shaft, the flexible tip portion comprising a flexible framework. The flexible framework can include a first inboard arm, second inboard arm, first outboard arm, and second outboard arm, wherein the flexible framework further includes a top face and a bottom face. A plurality of curved electrodes can be disposed about a longitudinal axis of each one of the first inboard arm, second inboard arm, first outboard arm, and second outboard arm, wherein each one of the plurality of curved electrodes is wrapped about an arm longitudinal axis of a respective one of the arms.

Various embodiments herein provide a medical device that comprises a catheter shaft. The catheter shaft can include a proximal end and a distal end. The catheter shaft can define a catheter shaft longitudinal axis. The medical device can include a flexible tip portion located adjacent to the distal end of the catheter shaft, the flexible tip portion comprising a flexible framework. The flexible framework can include a first inboard arm, second inboard arm, first outboard arm, and second outboard arm, wherein each of the arms is disposed through a tube. The medical device can include a plurality of microelectrodes disposed on each one of the tubes, the plurality of microelectrodes forming a flexible array of microelectrodes adapted to conform to tissue.

DETAILED DESCRIPTION

The contents of International Application No. PCT/US2014/011940 entitled Flexible High-Density Mapping Catheter Tips and Flexible Ablation Catheter Tips with Onboard High-Density Mapping Electrodes is hereby incorporated by reference as though fully set forth herein. The contents of U.S. application Ser. No. 15/331,562 entitled High Density Electrode Mapping Catheter and U.S. Application No. 62/572,186 entitled Catheter with High-Density Mapping Electrodes are hereby incorporated by reference as though fully set forth herein.

Figure 1A:
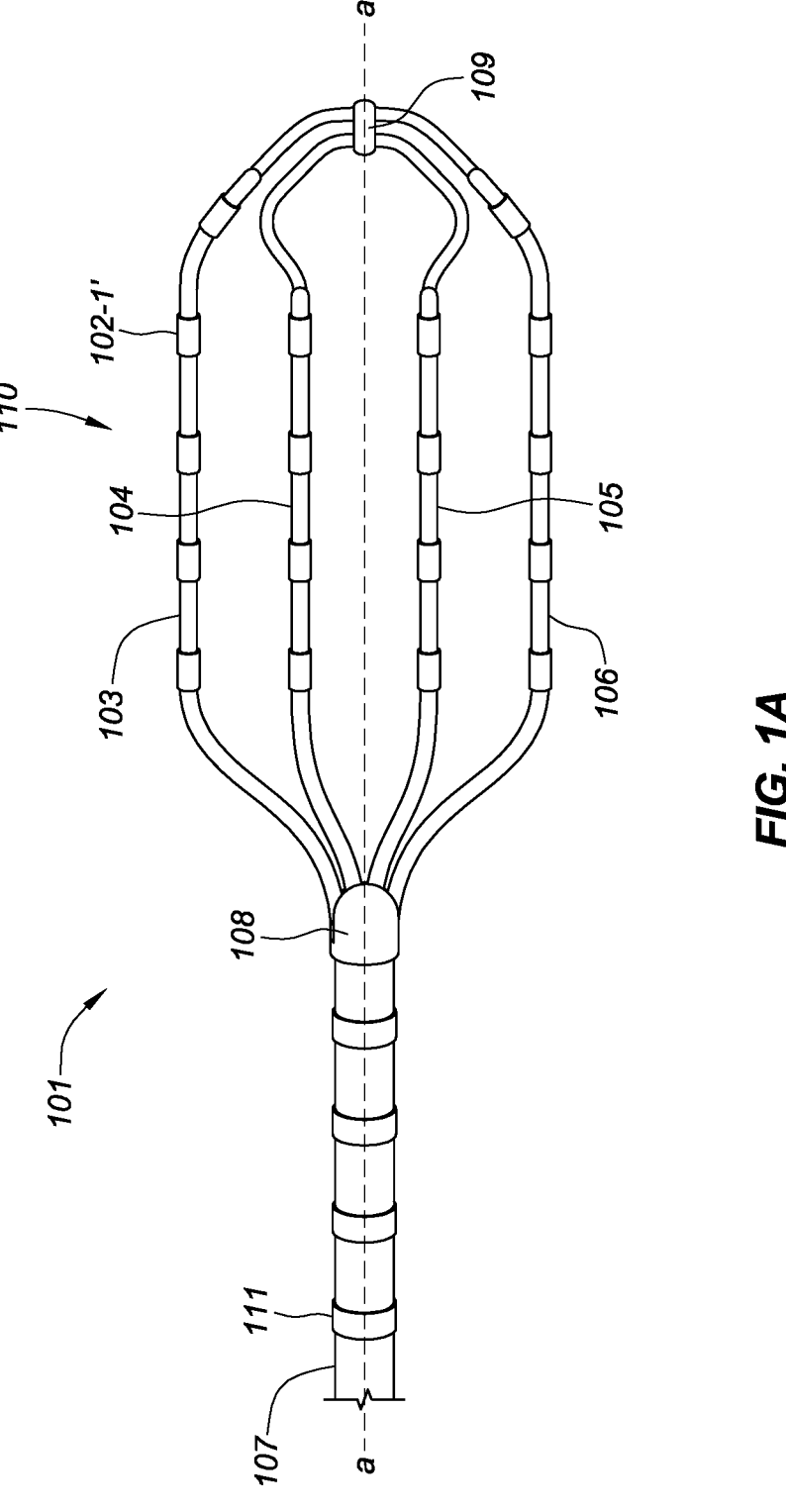
FIG. 1A depicts a top view of a high density electrode mapping catheter, according to various embodiments of the present disclosure.
Figures 1B, 1C:
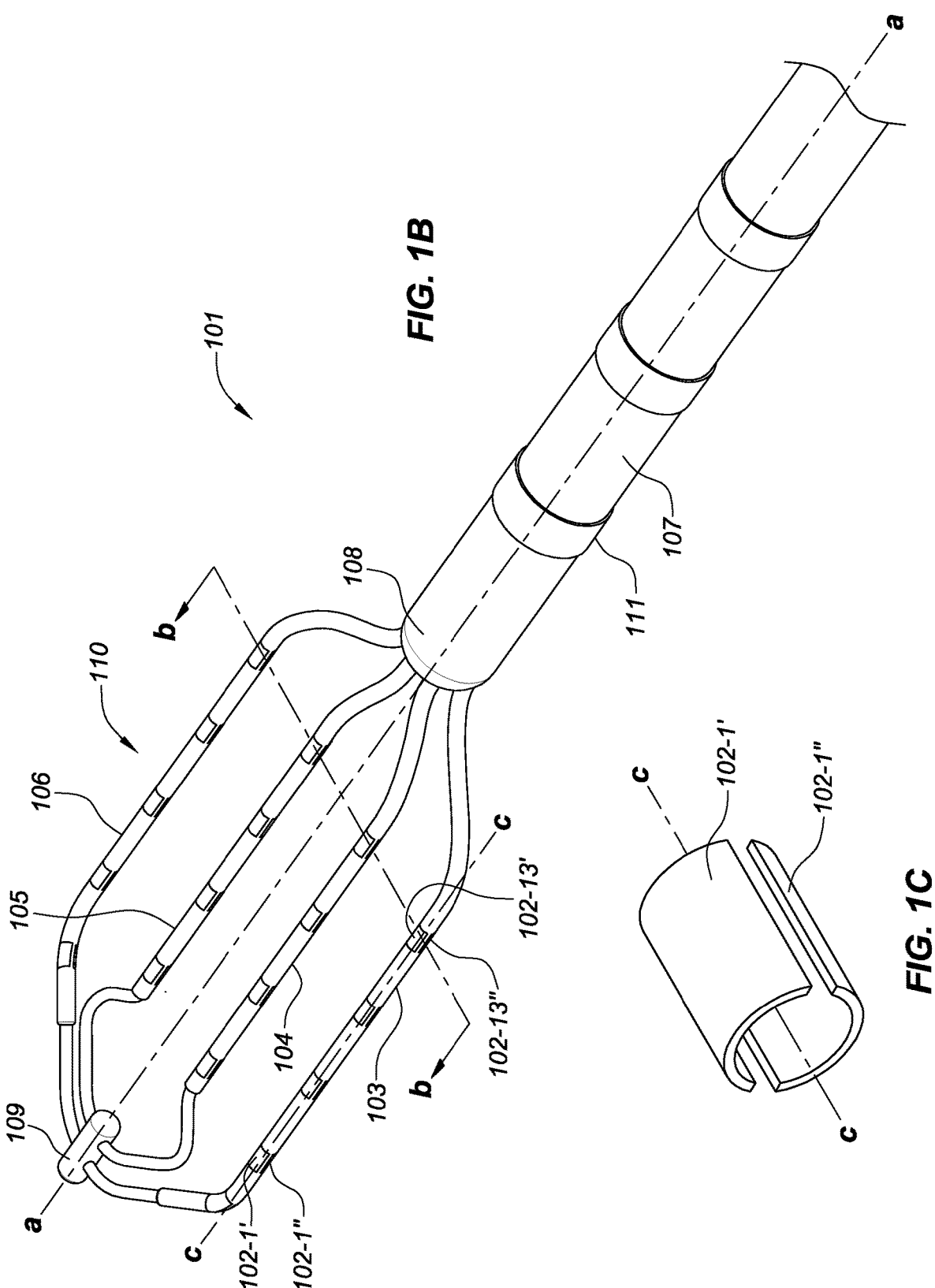
FIG. 1B depicts an isometric side and top view of the high density electrode mapping catheter in FIG. 1A, according to various embodiments of the present disclosure.
FIG. 1C depicts an isometric side, top, and distal end view of an electrode disposed on a flexible framework of the high density electrode mapping catheter depicted in FIGS. 1A and 1B, according to various embodiments of the present disclosure.

FIG. 1A depicts a top view of a high density electrode mapping catheter 101 and FIG. 1B is an isometric side and top view of the high density electrode mapping catheter 101, according to various embodiments of the present disclosure. In some embodiments, the high density electrode mapping catheter 101 can include a flexible tip portion 110 that forms a flexible array of electrodes. Although the high density electrode mapping catheter 101 includes a plurality of electrodes, for the sake of clarity, only electrodes 102-1', 102-1", 102-13', 102-13", also referred to herein as micro-electrodes, have been labeled in FIG. 1B. Hereinafter, electrodes 102-1' are referred to in the plural as electrodes 102. This planar array (or 'paddle' configuration) of electrodes 102 comprises four side-by-side, longitudinally-extending arms 103, 104, 105, 106, which can form a flexible framework on which the electrodes 102 are disposed. The four electrode-carrier arms comprise a first outboard arm 103, a second outboard arm 106, a first inboard arm 104, and a second inboard arm 105. These arms can be laterally separated from each other.

Each of the four arms can carry a plurality of electrodes 102. For example, each of the four arms can carry electrodes 102 spaced along a length of each of the four arms. Although each of the high density electrode mapping catheters 101 depicted in FIGS. 1A and 1B depict four arms, the high density electrode mapping catheters 101 could comprise more or fewer arms. Additionally, while the high density electrode mapping catheter 101 depicted in FIGS. 1A and 1B depict 16 electrodes disposed on a top half, also referred to herein as top portion or top face, of the flexible tip portion 110 (e.g., 4 electrodes on a top half of the first outboard arm 103 and second outboard arm 106 and 4 electrodes on a top half of the first inboard arm 104 and second inboard arm 105) and 16 electrodes disposed on a bottom half, also referred to herein as bottom portion or bottom face, of the flexible tip portion 110, as depicted in FIG. 1B (e.g., 4 electrodes on a bottom half of the first outboard arm 103 and second outboard arm 106 and 4 electrodes on a bottom half of the first inboard arm 104 and second inboard arm 105) catheters can include more or fewer than 16 electrodes disposed on the top half and/or more or fewer than 16 electrodes disposed on the bottom half. In addition, the first outboard arm 103 and second outboard arm 106 can include more or fewer than 4 electrodes disposed on the top half and/or bottom half and the first inboard arm 104 and second inboard arm 105 can include more or fewer than 4 electrodes disposed on the top half and/or bottom half.

In some embodiments, the electrodes 102 can be used in diagnostic, therapeutic, and/or mapping procedures. For example and without limitation, the electrodes 102 can be used for electrophysiological studies, pacing, cardiac mapping, and ablation. In some embodiments, the electrodes 102 can be used to perform unipolar or bipolar ablation. This unipolar or bipolar ablation can create specific lines or patterns of lesions. In some embodiments, the electrodes 102 can receive electrical signals from the heart, which can be used for electrophysiological studies. In some embodiments, the electrodes 102 can perform a location or position sensing function related to cardiac mapping.

In some embodiments, the high density electrode mapping catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis aa, as depicted in FIG. 1A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example.

The flexible tip portion 110 can be adapted to conform to tissue (e.g., cardiac tissue). For example, when the flexible tip portion 110 contacts tissue, the flexible tip portion can deflect, allowing the flexible framework to conform to the tissue. In some embodiments, the arms (or the understructure of the arms) comprising the paddle structure (or multiarm, electrode-carrying, flexible framework) at the distal end of the catheters depicted in FIGS. 1A and 1B are preferably constructed from a flexible or spring-like material such as Nitinol and/or a flexible substrate, as discussed herein. The construction (including, for example, the length and/or diameter of the arms) and material of the arms can be adjusted or tailored to be created, for example, desired resiliency, flexibility, foldability, conformability, and stiffness characteristics, including one or more characteristics that may vary from the proximal end of a single arm to the distal end of that arm, or between or among the plurality of arms comprising a single paddle structure. The foldability of materials such as Nitinol and/or flexible substrate provide the additional advantage of facilitating insertion of the paddle structure into a delivery catheter or introducer, whether during delivery of the catheter into the body or removal of the catheter from the body at the end of a procedure.

Among other things, the disclosed catheters, with their plurality of electrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the electrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted herein may be used in an epicardial procedure where the planar array of electrodes is positioned between the myocardial surface and the pericardium. Alternatively, the planar array embodiments may be used in an endocardial procedure to quickly sweep and/or analyze the inner surfaces of the myocardium and quickly create high-density maps of the heart tissue's electrical properties.

FIG. 1B depicts an isometric side and top view of the high density electrode mapping catheter 101 in FIG. 1A, according to various embodiments of the present disclosure. As depicted in FIG. 1B, the high density electrode mapping catheter 101 can include a catheter shaft 107 that includes a proximal end and a distal end. The catheter shaft 107 can define a catheter shaft longitudinal axis aa along which a flexible tip portion 110 distally extends from the distal end of the catheter shaft 107. In an example, the flexible tip portion 110 can be located adjacent to the distal end of the catheter shaft 107, the flexible tip 110 portion comprising a flexible framework, as previously discussed. The flexible framework can include a first inboard arm 104, second inboard arm 105, first outboard arm 103, and second outboard arm 106.

In some embodiments, a plurality of curved electrodes 102 can be disposed on the flexible framework 110 and can form a flexible array of curved electrodes 102 adapted to conform to tissue. In embodiments disclosed in FIG. 1B and further discussed herein and depicted in the figures, the curved electrodes 102 can be segmented electrodes. For example, the curved electrodes 102 may not extend around an entire circumference of the flexible framework 110 on which they are disposed, as depicted in FIGS. 1B to 2B. In an example, with reference to curved electrode pair 102-1' and 102-1", a first plurality of electrodes can be disposed on a bottom half of the flexible framework 110, for example, such as bottom curved electrode 102-1" and a second plurality of electrodes can be disposed on a top half of the flexible framework 110, such as top curved electrode 102-1'. Each of the first inboard arm 104, second inboard arm 105, first outboard arm 103, and second outboard arm 106 can extend along a respective arm longitudinal axis, each of which can be parallel with the catheter shaft longitudinal axis aa. In some embodiments, each of the respective arms can be divergent or convergent with the catheter shaft longitudinal axis aa. For example, as depicted in FIG. 1B, an arm longitudinal axis cc of the first outboard arm 103, as well as the other arms 104, 105, 106, can be parallel with the catheter shaft longitudinal axis aa. In some embodiments, the curved electrode pair 102-1' and 102-1" can be used in conjunction with omnipolar technology (OT), as described, for example, in U.S. Pat. No. 9,808,171 and U.S. Publication No. 2017/0042449, which are hereby incorporated by reference as though fully set forth herein.

In some embodiments, the plurality of curved electrodes 102 are disposed on each one of the first inboard arm 104, second inboard arm 105, first outboard arm 103, and second outboard arm 106 and are longitudinally spaced apart from one another, as depicted in FIG. 1B. In an example, the first inboard arm 104, second inboard arm 105, first outboard arm 103, and second outboard arm 106 can each include a top half and a bottom half on which curved electrodes 102-1', 102-1" can be disposed. For example, a plurality of corresponding pairs of curved electrodes can be disposed on each one of the arms 103, 104, 105, 106. Each one of the corresponding pairs of curved electrodes can include a top curved electrode and a bottom curved electrode that is disposed opposite to and below the top curved electrode on a respective one of the arms 103, 104, 105, 106. However, in some embodiments, the curved electrodes disposed on a top face of each one of the arms 103, 104, 105, 106 can be longitudinally staggered from respective curved electrodes disposed on a bottom face of each one of the arms 103, 104, 105, 106.

In some embodiments, at least one of the plurality of curved electrodes can be disposed on the top half and at least one of the plurality of curved electrodes can be disposed on the bottom half. In some embodiments, each one of the curved electrodes can be partially wrapped about an arm longitudinal axis of a particular one of the arms upon which the curved electrode is disposed. For example, as depicted with respect to the top and bottom curved electrodes 102-1', 102-1", the curved electrodes can be wrapped and/or revolved about the arm longitudinal axis cc. In some embodiments, the top curved electrode 102-1' and the bottom curved electrode 102-1" can form a curved electrode pair.

As depicted in FIG. 1C, each one of the top curved electrode 102-1' and the bottom curved electrode 102-1" are partially wrapped around the arm longitudinal axis cc. In an example, each of the at least one of the top curved electrodes disposed on the top half of the arm can be disposed opposite of a respective one of the bottom curved electrodes disposed on the bottom half of the arm to form a corresponding pair of curved electrodes. As further discussed herein, an amount by which the top curved electrode 102-1' and the bottom curved electrode 102-1" are wrapped around the arm longitudinal axis cc can vary.

As further depicted in FIG. 1C, the top curved electrode 102-1' can be circumferentially spaced apart from the bottom curved electrode 102-1". In some embodiments, a circumferential width of the top curved electrode 102-1' can be the same as a circumferential width of the bottom curved electrode 102-1", as depicted with respect to FIG. 1C and further discussed herein. However, in some embodiments, the circumferential width of the top curved electrode 102-1' can be different than the circumferential width of the bottom curved electrode 102-1", as depicted with respect to FIG. 1C and further discussed herein. Furthermore, a circumferential spacing between the top electrode 102-1' and the bottom electrode 102-1" can be the same.

In some embodiments, each of the first inboard arm 104, second inboard arm 105, first outboard arm 103, and second outboard arm 106 can include a plurality of corresponding pairs of curved electrodes 102. A first portion of the plurality of curved electrodes 102 can be disposed on a top of the flexible framework 110 and a second portion of the plurality of curved electrodes 102 can be disposed on a bottom of the flexible framework 110. In some embodiments, the placement of the plurality of curved electrodes 102 can be varied, as well as a circumferential width, longitudinal length, and/or thickness of the plurality of curved electrodes 102, as further discussed herein.

Figure 1D:
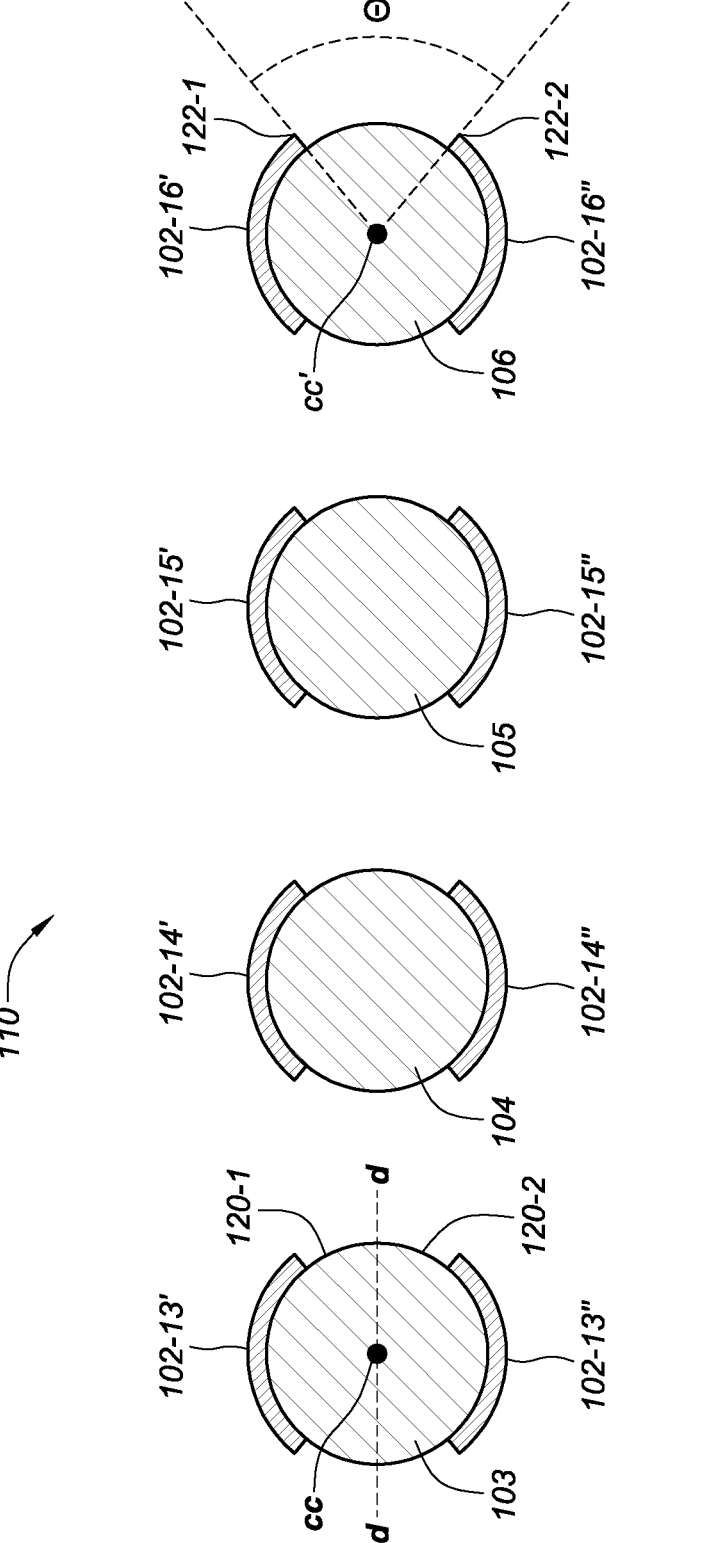
FIG. 1D depicts a cross-sectional end view of a plurality of curved electrodes disposed on a flexible framework, in accordance with embodiments of the present disclosure.

FIG. 1D depicts a cross-sectional end view of a plurality of curved electrodes 102 disposed on a flexible framework 110, in accordance with embodiments of the present disclosure. The flexible framework 110 can include a first outboard arm 103, a second outboard arm 106, a first inboard arm 104, and a second inboard arm 105. Although the cross-section of the first outboard arm 103, second outboard arm 106, first inboard arm 104, and second inboard arm 105 are depicted as solid in FIG. 1D, as well as FIGS. 2A to 2C, the respective cross-sections can be hollow. For example, the arms of the flexible framework 110 can be tubular structures. As depicted with respect to the first outboard arm 103, the arm can be divided into a top half 120-1 and a bottom half 120-2 via a horizontal axis dd; and the first outboard arm 103 can longitudinally extend along the arm longitudinal axis cc. In some embodiments, a top curved electrode 102-13' can be disposed on the top half 120-1 and a bottom curved electrode 102-13" can be disposed on the bottom half 120-2. As depicted in FIG. 1D, the top curved electrode 102-13' can be diametrically opposed to the bottom curved electrode, such that an equal circumferential spacing is defined between each one of the top curved electrode 102-13' and the bottom curved electrode 102-13".

The circumferential spacing defined between the top curved electrode 102-13' and the bottom curved electrode 102-13" can be larger and/or smaller than that depicted in FIG. 1D. In an example, the circumferential spacing defined between the top curved electrode 102-13' and the bottom curved electrode 102-13" can be in a range from 1 millimeter to 0.25 millimeters. In some embodiments, the spacing defined between the top curved electrode 102-13' and the bottom curved electrode 102-13" can be in a range from 0.75 millimeter to 0.5 millimeters. In some embodiments, the spacing between the circumferential edges of each one of the top curved electrodes and the bottom curved electrodes can be defined by an angle that exists between the circumferential edges of each one of the top curved electrode 102-16' and the bottom curved electrode 102-16" and the central axis cc' along which the second outboard arm 106 longitudinally extends. For example, the angle $\Theta^1$ is defined between the central axis cc' and the top outboard edge 122-1 of the top curved electrode 102-16' and the bottom outboard edge 122-2 of the bottom curved electrode 102-16". As depicted with respect to FIG. 1D, the angle $\Theta^1$ can be approximately 80 degrees. However, the angle $\Theta^1$ can be greater than or less than 80 degrees in some embodiments.

Figure 2A:
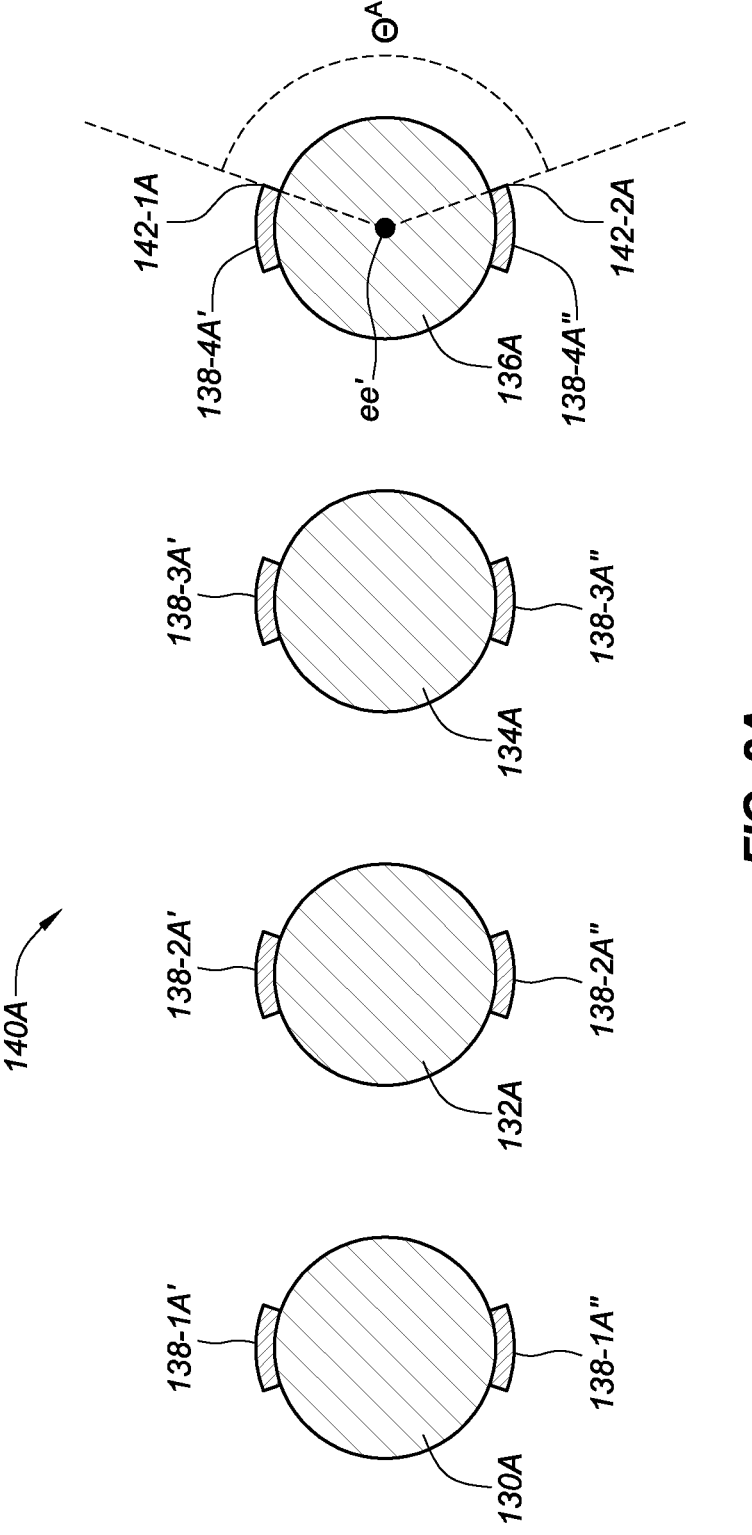
FIG. 2A is a cross-sectional end view of a plurality of curved electrodes, disposed on a flexible framework, wherein a defined spacing between a top curved electrode and bottom curved electrode is increased over the spacing depicted in FIG. 1D, in accordance with embodiments of the present disclosure.

FIG. 2A is a cross-sectional end view of a plurality of curved electrodes 138-1A', 138-1A", 138-2A', 138-2A", 138-3A', 138-3A", 138-4A', 138-4A" disposed on a flexible framework 140A, wherein a defined spacing between a top curved electrode and bottom curved electrode is increased over the spacing depicted in FIG. 1D, in accordance with embodiments of the present disclosure. Hereinafter, the plurality of curved electrodes 138-1A', 138-1A", 138-2A', 138-2A", 138-3A', 138-3A", 138-4A', 138-4A" are referred to in the plural as curved electrodes 138A. As depicted in FIG. 2A, the circumferential space defined between the top curved electrodes 138-1A', 138-2A', 138-3A', 138-4A' and the bottom curved electrodes 138-1A", 138-2A", 138-3A", 138-4A" can be increased. Accordingly, an angle $\Theta^A$ defined, for example, between a central longitudinal axis ee' along which the second outboard arm extends and the outboard edge 142-1A of the top curved electrode 138-4A' and the outboard edge 142-2A of the bottom curved electrode 142-2A" can be increased over that discussed and depicted in relation to FIG. 1D. As depicted in FIG. 2A, the angle $\Theta^A$ is approximately 135 degrees. However, the angle $\Theta^A$ can be greater than or less than 135 degrees in some embodiments. Although the second outboard arm 136A is discussed, the other arms include the same or similar features.

Figure 2B:
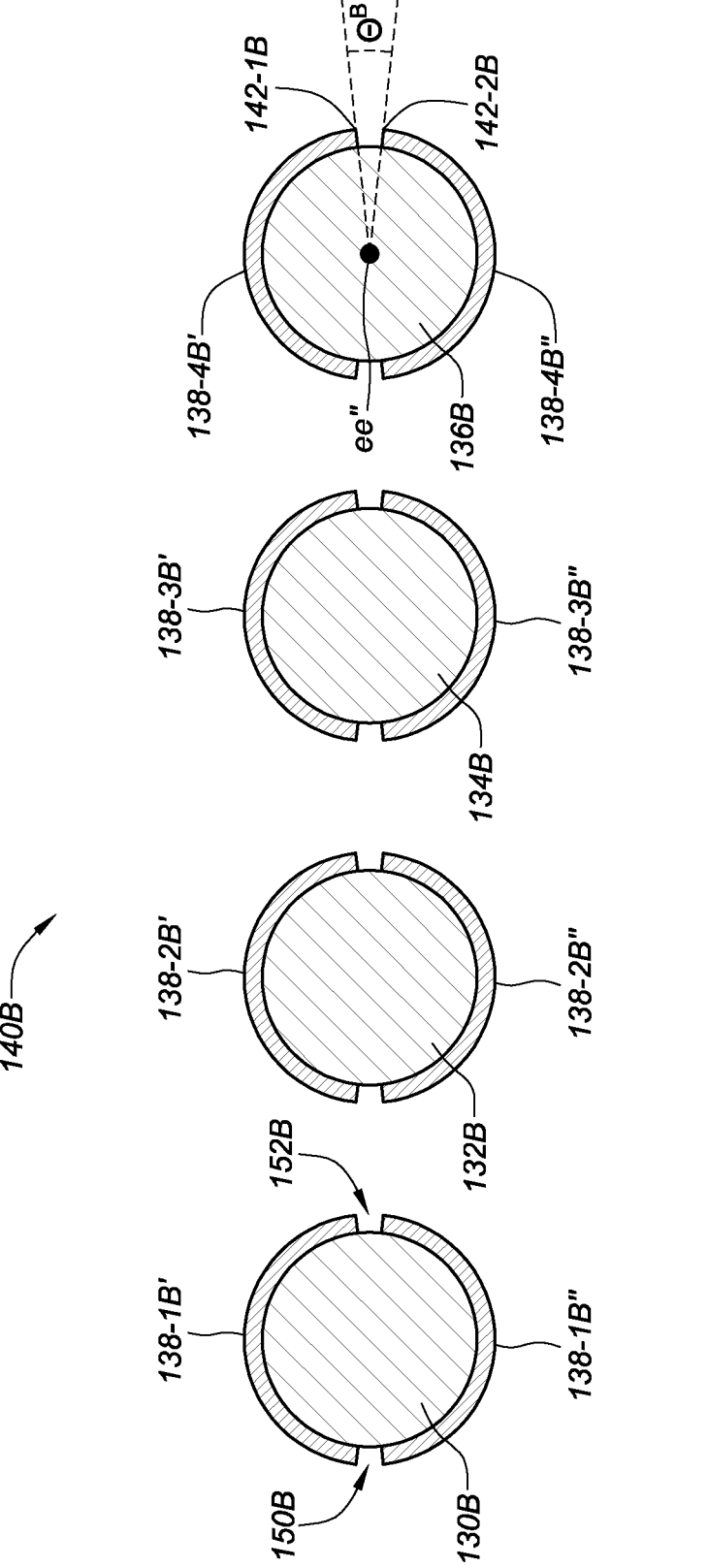
FIG. 2B is a cross-sectional end view of a plurality of curved electrodes, disposed on a flexible framework, wherein a defined spacing between a top curved electrode and bottom curved electrode is decreased over the spacing depicted in FIG. 1D, in accordance with embodiments of the present disclosure.

FIG. 2B is a cross-sectional end view of a plurality of curved electrodes 138-1B', 138-1B", 138-2B', 138-2W, 138-3B', 138-3B", 138-4B', 138-4B", disposed on a flexible framework 140B, wherein a defined spacing between a top curved electrode and bottom curved electrode is decreased over the spacing depicted in FIG. 1D, in accordance with embodiments of the present disclosure. As depicted in FIG. 2B, a pair of circumferential gaps 150B, 152B can be defined between the first top curved electrode 138-1B' and the first bottom curved electrode 138-1B". In some embodiments, each one of the curved electrodes 138B can have a decreased radial thickness from what is shown in relation to FIG. 2B, such that a radial depth of the circumferential gaps 150B, 152B is minimized. In some embodiments, the circumferential gaps 150B, 152B can be filled with an insulative material. In an example, the circumferential gaps 150B, 152B can be filled such that an exterior surface of the component formed by the arm 130B and the top curved electrode 138-1B' and the bottom curved electrode 138-1B" can be one continuous surface. For example, the outer surface of the component can be smooth and uninterrupted.

As further depicted with respect to FIG. 2B, the circumferential space defined between the top curved electrodes 138-1B', 138-2B', 138-3B', 138-4B' and the bottom curved electrodes 138-1B", 138-2B", 138-3B", 138-4B" can be decreased with respect to FIGS. 1D and 2A. Accordingly, an angle $\Theta^B$ defined between a central axis ee" along which the second outboard arm 136B extends and the top outboard edge 142-1B of the top curved electrode 138-4B' and the bottom outboard edge 142-2B of the bottom curved electrode 138-4B" can be increased over that discussed and depicted in relation to FIGS. 1D and 2A. As depicted in FIG. 2B, the angle $\Theta^B$ is approximately 20 degrees. However, the

9 angle $\Theta^B$ can be greater than or less than 20 degrees in some embodiments. As depicted with respect to FIGS. 1D to 2B, the top curved electrodes can be diametrically opposed to the bottom curved electrodes. Further, the top curved electrodes can have a same circumferential width as the bottom curved electrodes. However, as depicted in FIG. 2C, in some embodiments, the top curved electrode can have a smaller or larger circumferential width than the bottom curved electrode.

Figure 2C:
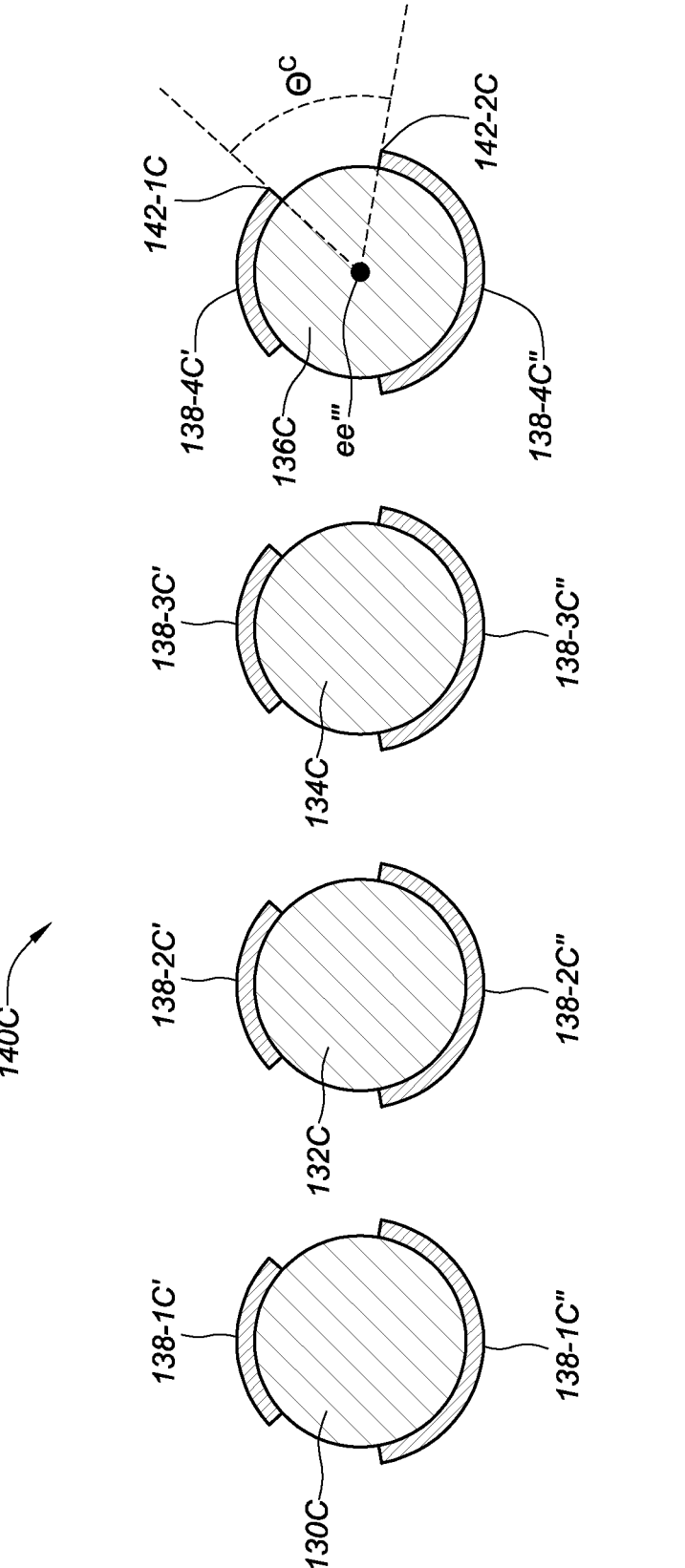
FIG. 2C is a cross-sectional end view of a plurality of curved electrodes, disposed on a flexible framework, wherein a circumferential width of the top curved electrode is less than a circumferential width of the bottom curved electrode, in accordance with embodiments of the present disclosure.

FIG. 2C is a cross-sectional end view of a plurality of curved electrodes 138-1C', 138-1C", 138-2C', 138-2C", 138-3C', 138-3C", 138-4C', 138-4C", disposed on a flexible framework 140C, wherein a circumferential width of the top curved electrode is less than a circumferential width of the bottom curved electrode, in accordance with embodiments of the present disclosure. Each one of the plurality of curved electrodes 138-1C', 138-1C", 138-2C', 138-2C", 138-3C', 138-3C", 138-4C', 138-4C" is wrapped around a longitudinal axis (i.e., ee''') of a respective one of the first outboard arm 130C, first inboard arm 132C, second inboard arm 134C, and second outboard arm 136C. As depicted in FIG. 2C, a circumferential gap can be defined between the top curved electrode 138-4C' and the bottom curved electrode 138-4C". For instance, the gap can be defined between the top outboard edge 142-1C of the top curved electrode 138-4C' and the bottom outboard edge 142-2C of the bottom curved electrode 138-4C". In some embodiments, the top curved electrodes 138-1C', 138-2C', 138-3C', and the bottom curved electrodes 138-1C", 138-2C", 138-3C" can have a same gap between their outboard edges. In some embodiments, an equal gap can be defined between the inboard edges of the top curved electrodes 138-1C', 138-2C', 138-3C', 138-4C', and the bottom curved electrodes 138-1C", 138-2C", 138-3C", 138-4C", as that discussed in relation to the outboard edges. However, in some embodiments, a defined gap between the inboard edges and the outboard edges can be different with respect to one another.

In some embodiments, an angle $\Theta^C$ can be defined between a central axis ee''', for example, along which the second outboard arm 136C extends and the top outboard edge 142-1C of the top curved electrode 138-4C' and the bottom outboard edge 142-2C of the bottom curved electrode 138-4C", as similarly discussed in relation to FIGS. 1D-2B. As depicted in FIG. 2C, the angle $\Theta^C$ is approximately 60 degrees. However, the angle $\Theta^C$ can be greater than or less than 20 degrees in some embodiments. For example, in some embodiments, a circumferential width of the top curved electrode 138-4C' can be increased or decreased over what is depicted in FIG. 2C, thus decreasing or increasing the angle $\Theta^C$. In some embodiments, the circumferential width of the bottom electrode 138-4C" can be increased or decreased over what is depicted in FIG. 2C, thus decreasing or increasing the angle $\Theta^C$.

Figure 3A:
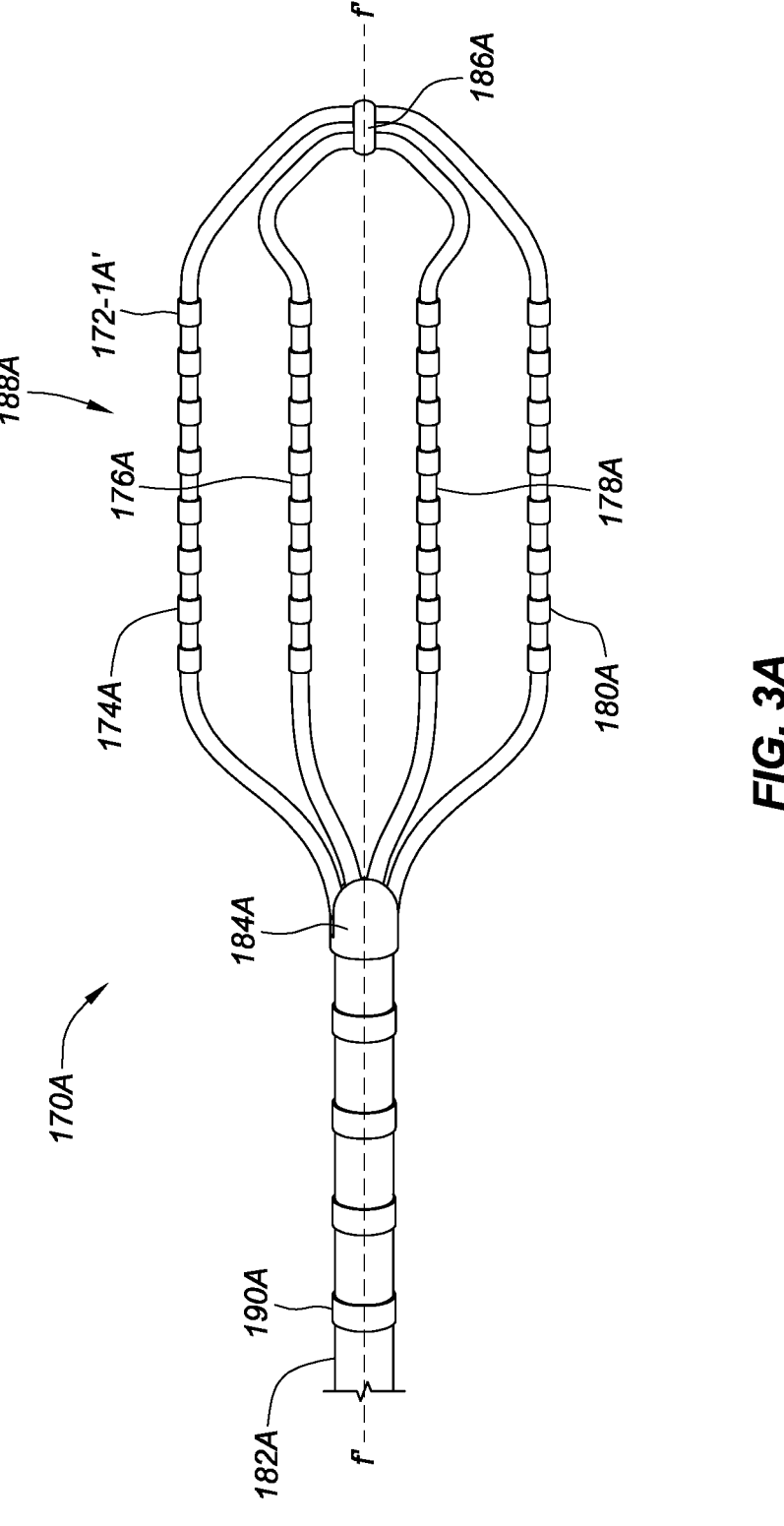
FIG. 3A depicts a top view of a high density electrode mapping catheter that includes 32 pairs of top curved electrodes and bottom curved electrodes, according to various embodiments of the present disclosure.

FIG. 3A depicts a top view of a high density electrode mapping catheter 170A that includes 32 pairs of top curved electrodes and bottom curved electrodes (not depicted), according to various embodiments of the present disclosure. The high density electrode mapping catheter 170A can include a catheter shaft 182A, along which are disposed a plurality of ring electrodes 190A. A distal end of the catheter shaft 182A can include a connector, from which a plurality of longitudinally-extending arms 174A, 176A, 178A, 180A extend. The high density electrode mapping catheter 170A can extend along a longitudinal axis ff. In some embodiments, the high density electrode mapping catheter 170A can include a flexible tip portion 188A that forms a flexible array of electrodes. Although the high density electrode mapping catheter 170A includes a plurality of electrodes, for the sake of clarity, only top curved electrode 172-1A' has been labeled in FIG. 3A. Although the bottom curved electrodes are not visible in FIG. 3A, the top curved electrodes 172-1A' and the bottom curved electrodes can be disposed on the four side-by-side, longitudinally-extending arms 174A, 176A, 178A, 180A, which can form a flexible framework 188A on which the electrodes 172A are disposed.

The top curved electrodes 172A and the bottom curved electrodes can be disposed along the longitudinally-extending arms in a manner similarly to that discussed herein, for example in relation to FIGS. 1D-2C. The four electrode-carrier arms comprise a first outboard arm 174A, a second outboard arm 180A, a first inboard arm 176A, and a second inboard arm 178A. These arms can be laterally separated from each other. Each of the four arms can carry a plurality of electrodes 172A. For example, as depicted in FIG. 3A, each one of the four arms can have eight curved electrodes 172A disposed along a top of each arm. Additionally, each one of the four arms can have eight curved electrodes disposed along a bottom of each arm. For example, a total of 32 pairs of curved electrodes can be disposed on the flexible tip portion 188A of the high density electrode mapping catheter 170A, providing for a total of 64 electrodes disposed on the top and bottom of the longitudinally-extending arms. A pair of curved electrodes can include a top curved electrode and a corresponding bottom curved electrode in some embodiments. For example, as discussed herein, the top curved electrodes can be diametrically opposed to respective ones of the bottom curved electrodes.

Figure 3B:
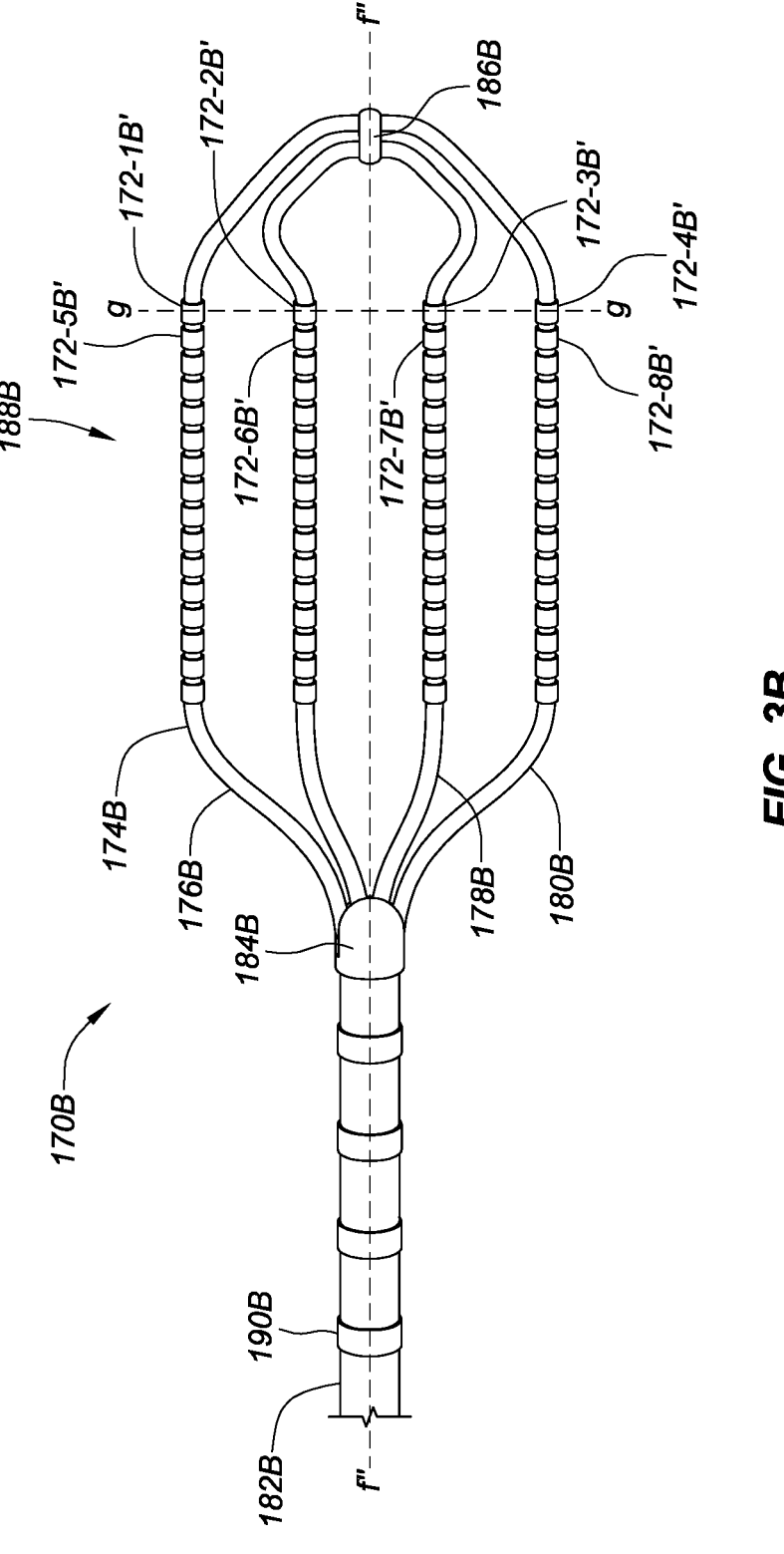
FIG. 3B depicts a top view of a high density electrode mapping catheter that includes 64 pairs of top curved electrodes and bottom curved electrodes, according to various embodiments of the present disclosure.

FIG. 3B depicts a top view of a high density electrode mapping catheter 170A that includes 64 pairs of top curved electrodes 172-1B', 172-2B', 172-3B', 172-4B', 172-5B', 172-6B', 172-7B', 172-8B' and bottom curved electrodes (not depicted), according to various embodiments of the present disclosure. The high density electrode mapping catheter 170B can include those features discussed in relation to FIG. 3A, with the exception that 64 pairs of curved electrodes 172 can be disposed on the flexible tip portion 188B of the high density electrode mapping catheter 170B. Thus, a total of 128 electrodes can be disposed on the top and bottom of the longitudinally extending arms. In some embodiments, as depicted, the top curved electrodes and the bottom curved electrodes can be disposed along each one of the longitudinally extending arms 174B, 176B, 178B, 180B and can also be aligned in rows of electrodes that are disposed transversely to the longitudinal axis ff. For example, the curved top electrodes 172-1B', 172-2B', 172-3B', 172-4B' can be disposed on each one of the longitudinally extending arms 174B, 176B, 178B, 180B along a line gg that is transverse to a catheter shaft longitudinal axis ff. Thus, the high density electrode mapping catheter 170B can include 16 rows of electrodes, as depicted in FIG. 3B.

In some embodiments, one or more of the electrodes can be deactivated, such that a pattern of active electrodes is created on the high density electrode mapping catheter 170B. For instance, a first top electrode 172-1B' can be turned off, as well as a third top electrode 172-3B', in addition to their corresponding bottom electrodes, thus leaving the second top electrode 172-1B' and the fourth top electrode 172-4W as active electrodes. Additionally, a sixth top electrode 172-6B' and an eighth top electrode 172-6W can be turned off, in addition to their corresponding bottom electrodes, thus leaving the fifth top electrode 172-5B' and the seventh top electrode 172-7W as active electrodes. In an example, an electrode can be deactivated (i.e., turned off) by electrically disconnecting the electrode from a central processing unit via a physical and/or virtual switch in some embodiments. Thus, measurements can be taken from the active electrodes and not the deactivated electrodes.

Figure 4A:
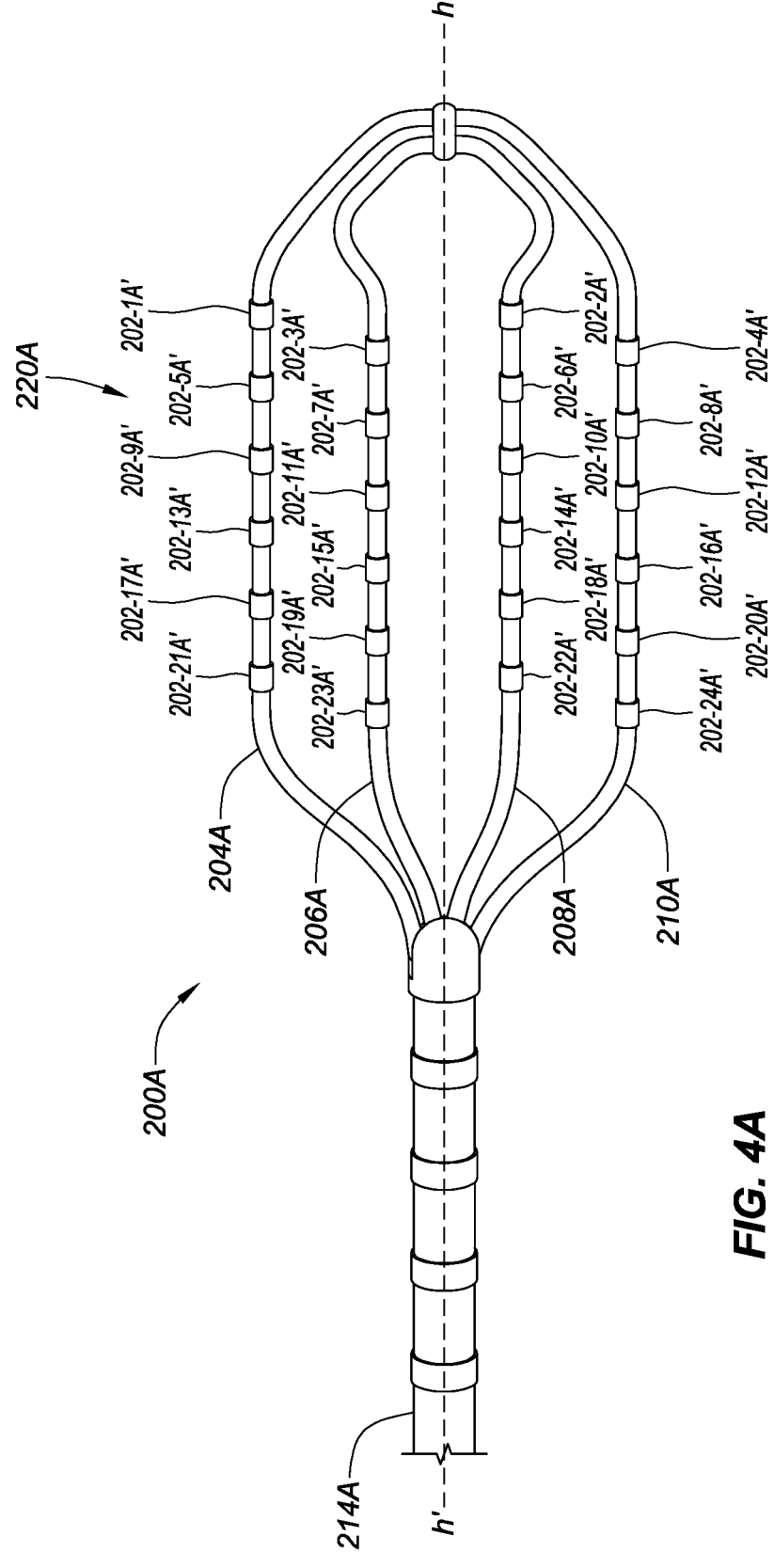
FIG. 4A depicts a top view of a high density electrode mapping catheter that includes 24 pairs of top curved electrodes and bottom curved electrodes disposed in an alternating arrangement, according to various embodiments of the present disclosure.

FIG. 4A depicts a top view of a high density electrode mapping catheter 200A that includes 24 pairs of top curved electrodes 202-1A', 202-2A', . . . 202-24A' and bottom curved electrodes (not depicted) disposed in an alternating arrangement, according to various embodiments of the present disclosure. In some embodiments, the top curved electrodes 202-1A', 202-2A', . . . 202-24A', hereinafter referred to in the plural as top curved electrodes 202A' and the bottom curved electrodes can be electrically connected with a central processing unit via a plurality of wires electrically coupled with each one of the top curved electrodes 202A' and the bottom curved electrodes. However, due to space restrictions within a lumen defined by each one of the first outboard arm 204A, first inboard arm 206A, second inboard arm 208A, and second outboard arm 210A, as well as a central lumen defined by the catheter shaft 214A, it can be difficult to fit respective wires that electrically couple each one of the electrodes into each one of the first outboard arm 204A, first inboard arm 206A, second inboard arm 208A, and second outboard arm 210A, as well as a central lumen defined by the catheter shaft 214A, which extends along the longitudinal axis hh'. Accordingly, in some embodiments, a pattern of electrodes can be arranged on a flexible tip portion 220A of the high density electrode mapping catheter 200A.

In an example, the pattern can include an alternating arrangement, wherein electrodes on each one of the arms are staggered. This can reduce the number of electrodes disposed on the flexible tip portion 220A and also reduce a number of electrical wires needed to electrically couple all of the electrodes. In an example, placement of the electrodes in the alternating arrangement, versus an arrangement such as that depicted in FIGS. 1A and 1B, can reduce the number of electrodes disposed on the flexible tip portion 220A and can reduce the number of wires connecting the electrodes by half. For instance, the arrangement of electrodes can include a checkerboard pattern in some embodiments, wherein a plurality of electrodes are longitudinally disposed along each one of the arms in a spaced apart relationship. In an example, a spacing of the electrodes can be staggered with respect to adjacent arms. For instance, with respect to the first outboard arm 204A, the top curved electrodes 202-1A', 202-5A', 202-9A', 202-13A', 202-17A', and 202-21A' can be disposed along the first outboard arm 204A in a spaced apart relationship. In an example, a spacing between each one of the top curved electrodes 202-1A', 202-5A', 202-9A', 202-13A', 202-17A', and 202-21A' can be the same.

With reference to the top curved electrodes 202-3A', 202-7A', 202-11A', 202-15A', 202-19A', and 202-23A' disposed on the first inboard arm 206A, the electrodes 202-3A', 202-7A', 202-11N, 202-15A', 202-19A', and 202-23A' can have a same spacing as the top curved electrodes 202-1A', 202-5A', 202-9A', 202-13A', 202-17A', and 202-21A' disposed on the first inboard arm 204A, however, a position of each one of the top curved electrodes 202-3A', 202-7A', 202-11A', 202-15A', 202-19A', and 202-23A' can be shifted proximally to form a checkerboard pattern. For instance, the most distal top curved electrode 202-3A' on the first inboard arm 206A can be longitudinally disposed at a position on the first inboard arm 206A between the top curved electrodes 202-1A' and 202-5A'. With reference to FIG. 4A, although only the top curved electrodes 202A' are depicted, the bottom curved electrodes can be disposed beneath each one of the top curved electrodes 202A' and have the same spacing as the top curved electrodes 202A'. Through placement of the electrodes in the alternating arrangement, such as that depicted in FIG. 4A, an adequate density of electrodes can be maintained, while reducing the overall number of electrodes, as well as electrical connections, which can reduce a complexity and cost of manufacturing, while still enabling the high density electrode mapping catheter 200A to accurately measure electrical signals generated by a cardiac tissue.

Figure 4B:
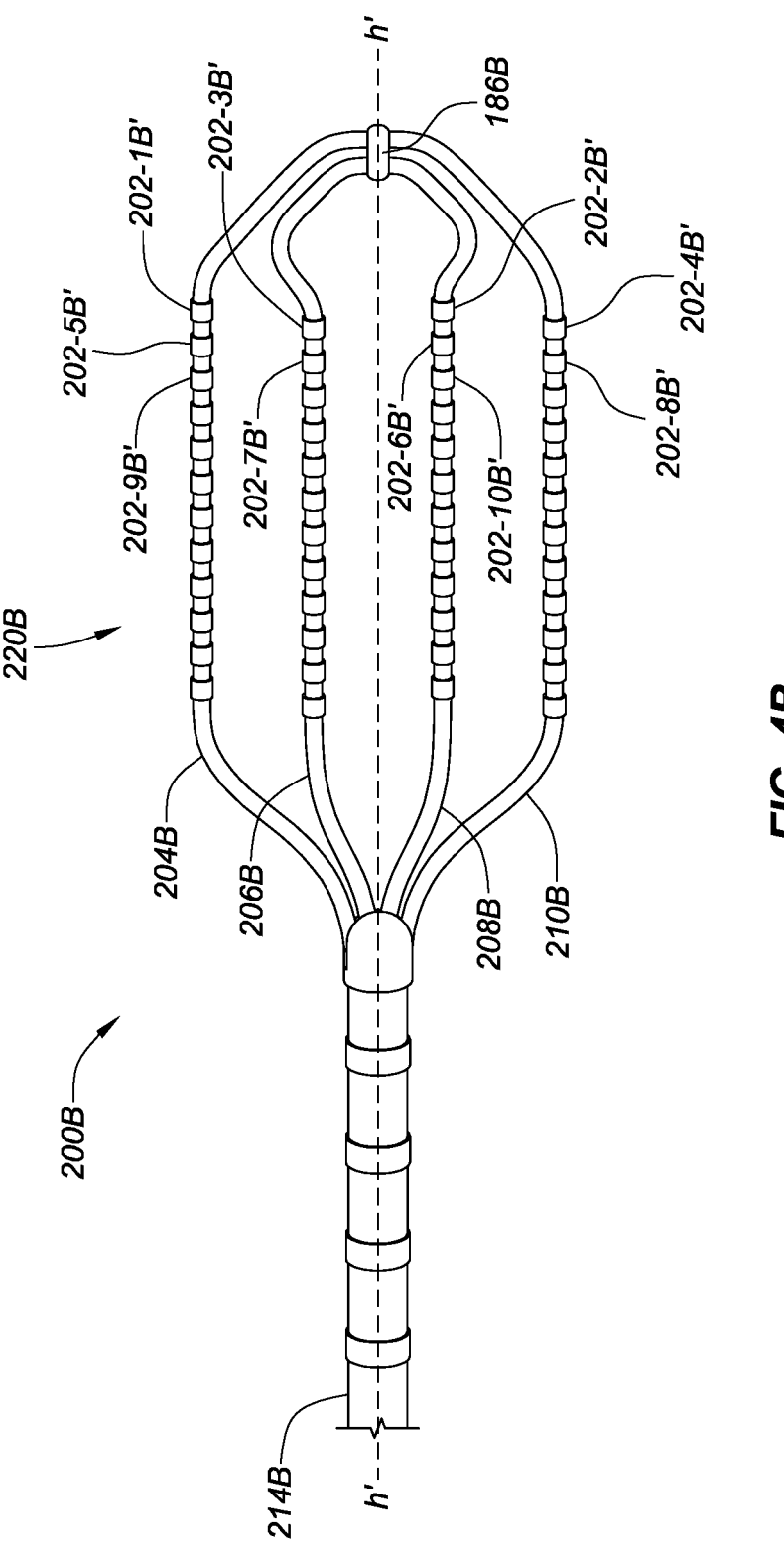
FIG. 4B depicts a top view of a high density electrode mapping catheter that includes 48 pairs of top curved electrodes and bottom curved electrodes disposed in an alternating arrangement, according to various embodiments of the present disclosure.

FIG. 4B depicts a top view of a high density electrode mapping catheter 200B that includes 48 pairs of top curved electrodes 202-1B', 202-2B', . . . 202-10B' and bottom curved electrodes (not depicted) disposed in an alternating arrangement, according to various embodiments of the present disclosure. Although the high density electrode mapping catheter 200B includes top curved electrodes, for clarity, only top curved electrodes 202-1B', 202-2B', . . . 202-10B' are labeled. In some embodiments, the top curved electrodes 202-1B', 202-2B', . . . 202-24B', hereinafter referred to in the plural as top curved electrodes 202B', and the bottom curved electrodes can be electrically connected with a central processing unit via a plurality of wires electrically coupled with each one of the top curved electrodes 202B' and the bottom curved electrodes. As discussed above, embodiments of the present disclosure can reduce an amount of space needed to house the plurality of wires that electrically couple each one of the top curved electrodes 202B' and bottom curved electrodes. In contrast to FIG. 4A, the flexible tip portion 220B includes double the number of electrodes versus the flexible tip portion 220A depicted in FIG. 4A. As previously mentioned, placement of the electrodes in the alternating arrangement, versus an arrangement such as that depicted in FIGS. 1A and 1B, can reduce the number of electrodes disposed on the flexible tip portion 220B and can reduce the number of wires connecting the electrodes by half. For example, the embodiments disclosed in FIG. 4B include 96 total electrodes disposed on the top half and bottom half of the flexible tip portion 220B.

In some embodiments, the arrangement of electrodes can include a checkerboard pattern, wherein a plurality of electrodes are longitudinally disposed along each one of the arms in a spaced apart relationship. In an example, a spacing of the electrodes can be staggered with respect to adjacent arms. For instance, with respect to the first outboard arm 204B, the top curved electrodes 202-1B', 202-5B', 202-9B', etc. can be disposed along the first outboard arm 204B in a spaced apart relationship. In an example, a spacing between each one of the top curved electrodes 202-1B', 202-5B', 202-9B', etc. can be the same. With reference to the top curved electrodes 202-3B', 202-7B', etc. disposed on the first inboard arm 206B, the top curved electrodes 202-3B', 202-7B', etc. can have a same spacing as the top curved electrodes 202-1B', 202-5B', 202-9B', etc. disposed on the first inboard arm 204B, however, a position of each one of the top curved electrodes 202-3B', 202-7B', etc. can be shifted proximally to form a checkerboard pattern. For instance, the most distal top curved electrode 202-3B' on the first inboard arm 206B can be longitudinally disposed at a position on the first inboard arm 206B between the top curved electrodes 202-1B' and 202-5B'.

Figure 5:
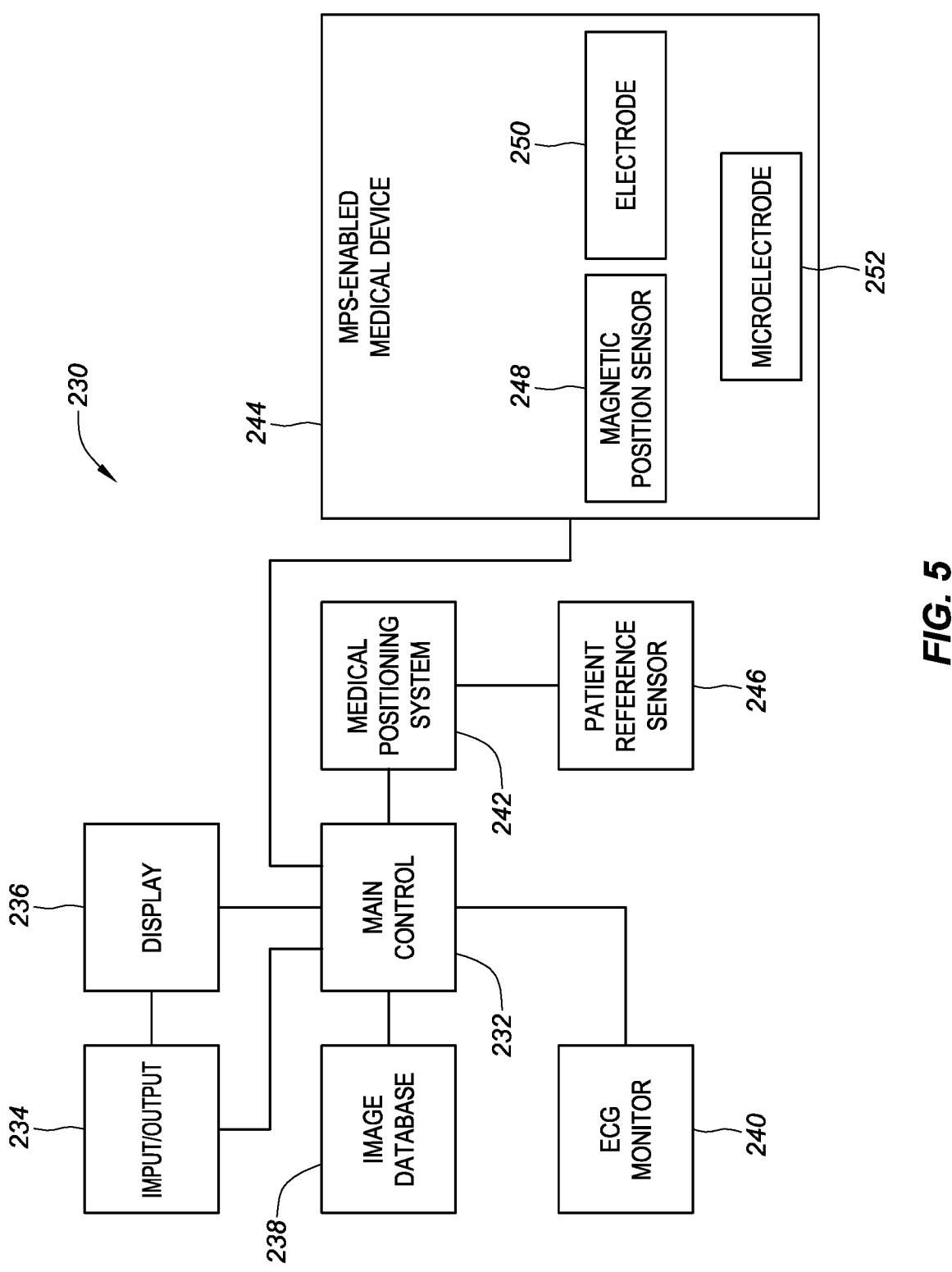
FIG. 5 depicts a schematic and block diagram view of a medical system, in accordance with embodiments of the present disclosure.

FIG. 5 depicts a schematic and block diagram view of a medical system 230, in accordance with embodiments of the present disclosure. System 230, as depicted, includes a main electronic control unit 232 (e.g., a processor) having various input/output mechanisms 234, a display 236, an optional image database 238, an electrocardiogram (ECG) monitor 240, a localization system, such as a medical positioning system 242, a medical positioning system-enabled elongate medical device 244, a patient reference sensor 246, a magnetic position sensor 248, an electrode 250 (e.g., position sensing electrode), and a microelectrode 252 configured to sense electrical signals produced by the heart. For simplicity, one magnetic position sensor 248, one electrode 250, and one microelectrode 252 are shown, however, more than one magnetic position sensor 248, more than one electrode 250, and/or more than one microelectrode 252 can be included in the system 230.

Input/output mechanisms 234 may comprise conventional apparatus for interfacing with a computer-based control unit including, for example, one or more of a keyboard, a mouse, a tablet, a foot pedal, a switch and/or the like. Display 236 may also comprise conventional apparatus, such as a computer monitor.

System 230 may optionally include image database 238 to store image information relating to the patient's body. Image information may include, for example, a region of interest surrounding a destination site for medical device 244 and/or multiple regions of interest along a navigation path contemplated to be traversed by medical device 244. The data in image database 238 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 240. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 240 is configured to continuously detect an electrical timing signal of the heart organ through the use of a plurality of microelectrodes 252. As discussed herein, the microelectrodes 252 can include the electrodes disposed on the flexible tip portions of the devices previously discussed herein, for example, in relation to FIGS. 1A to 4B. The timing signal generally corresponds to a particular phase of the cardiac cycle, among other things. Generally, the ECG signal(s) may be used by the control unit 232 for ECG synchronized play-back of a previously captured sequence of images (cine loop) stored in database 238. ECG monitor 240 and ECG-electrodes may both comprise conventional components. In some embodiments, the main control 232 can include a computing device, which can include hardware and/or a combination of hardware and programming that is configured to determine a difference in signals received by microelectrodes, as discussed herein. For example, the main control 232 can include a non-transitory computer readable medium that stores instructions, which are executable by a processor, in communication with the main control 232, to determine a difference in signals received from microelectrodes. Medical positioning system 244 is configured to serve as the localization system and therefore to determine position (localization) data with respect to one or more magnetic position sensors 248 and/or electrodes 250 and output a respective location reading.

In some embodiments, the main control can execute computer-readable instructions configured to disable particular ones of the electrodes and/or enable particular ones of the electrodes to form a particular pattern of electrodes disposed on a flexible tip portion of a high density electrode mapping catheter, as discussed in relation to FIGS. 3A to 4B and further discussed in U.S. application Ser. No. 15/331, 562 entitled High Density Electrode Mapping Catheter, which is hereby incorporated by reference as though fully set forth herein. Some embodiments of the present disclosure can include receiving a first electrical signal from the first electrode disposed on a first side of a tip portion of a medical device (e.g., high density electrode mapping catheter). The method can further include receiving a second electrical signal from a second electrode disposed on a second side of the tip portion of the medical device. As previously discussed, the first electrode and the second electrode can be disposed vertically adjacent with respect to one another. For example, the first electrode can be disposed directly beneath the second electrode, as depicted and discussed herein.

In some embodiments, the method can include determining a degree of contact between the first electrode and the tissue based on a comparison between the first electrical signal and the second electrical signal. In an example, when the first electrode is disposed against tissue, the second electrode can be disposed on the opposite side of the medical device and in a blood pool. As such, a different electrical signal (e.g., voltage) can be received from the first electrode versus the second electrode. Accordingly, in some embodiments, the comparison between the first electrical signal and the second electrical signal can include comparing a first voltage associated with the first electrical signal and a second voltage associated with the second electrical signal.

In an example, cardiac tissue can generate a voltage whenever it depolarizes. The voltage can propagate through the heart muscle and also through the blood pool and can be picked up by both the first electrode and the second electrode. If one of the electrodes (e.g., first electrode) is touching the tissue, then that voltage will be different than the voltage picked up by the electrode disposed in the blood pool (e.g., second electrode). The difference between the first electrical signal associated with the first electrode and the second electrical signal associated with the second electrode will be greater when the first electrode is touching the tissue and the second electrode is disposed in the blood pool. The difference between the first electrical signal associated with the first electrode and the second electrical signal associated with the second electrode will be smaller when the first electrode and second electrode are both disposed in the blood pool.

Based on the differences in electrical signals (e.g., voltages), a determination of contact between the medical device (e.g., first electrode) and the tissue can be made. For example, the method can include determining that the first electrode is not in contact with the tissue when the first voltage associated with the first electrical signal and the second voltage associated with the second electrical signal are the same. For example, when the voltages associated with the first electrode and the second electrode are the same, this can be an indication that the first electrode and the second electrode are disposed in the blood pool and are not in contact with the tissue. In some embodiments, the method can include determining that the first electrode is not in contact with the tissue when a difference between the first voltage associated with the first electrical signal and the second voltage associated with the second electrical signal is less than a threshold voltage (e.g., the voltages are close to being the same). For example, the voltages associated with each of the first and second electrodes may not be exactly the same due to electrical interference in the blood pool.

Alternatively, in some embodiments, the method can include determining that the first electrode is in contact with the tissue when the first voltage associated with the first electrical signal is different than the second voltage associated with the with the second electrical signal. In an example, the method can include determining that the first electrode is in contact with the tissue when a difference between the first voltage associated with the first electrical signal and the second voltage associated with the second electrical signal is greater than a threshold value. For instance, the method can include determining that the first electrode is in contact with the tissue when the first voltage associated with the first electrical signal is greater than the second voltage associated with the second electrical signal (e.g., is greater than a defined threshold value). As discussed, when the first electrode is disposed against the tissue and the second electrode is disposed in the blood pool, the first electrical signal associated with the first electrode can have a greater voltage than the second electrical signal.

In some embodiments, the method can include determining that a degree of contact between the first electrode and the tissue is increasing based on the first voltage associated with the first electrical signal being increased with respect to the second voltage associated with the second electrical signal. For example, if the first voltage associated with the first electrical signal increases at a greater rate than the second voltage associated with the second electrical signal and/or increases while the second voltage stays the same, a determination can be made that a degree of contact between the first electrode and the tissue is increasing. In some embodiments, ensuring that sufficient contact exists between the medical device and the tissue can be beneficial where diagnostic information is being collected by the medical device (e.g., electrodes) and/or therapeutic energy is being delivered to the tissue from the medical device (e.g., electrodes). Alternatively, the method can include determining that a degree of contact between the first electrode and the tissue is decreasing based on the first voltage associated with the first electrical signal being decreased with respect to the second voltage associated with the second electrical signal.

In some embodiments, the first and/or second electrode can be configured to be driven by an electrical current (e.g., high frequency electrical current). In an example, the first and/or second electrode can be driven with the electrical current and a voltage (e.g., high frequency voltage) can be induced by the electrical current. For instance, a voltage can be induced in the cardiac tissue and/or in the blood pool. Accordingly, an induced voltage, which is generated by one or more of the electrodes, rather than the heart, can be received by one or more of the electrodes on the medical device. The induced voltage (e.g., impedance) associated with an electrical signal received from one of the electrodes can be measured. Depending on whether an electrode from which the electrical signal is received is disposed in the blood pool or is in contact with the tissue, the electrical signal can vary. In an example, the induced voltages that are measured from an electrical signal received from the first electrode and the second electrode can be different if one of the electrodes is disposed against tissue and one of the electrodes is disposed in the blood pool and can be similar if both electrodes are disposed in the blood pool.

In some embodiments, one or both of the first electrode and the second electrode can be driven with the current and one or more other electrodes disposed on the medical device or an electrode disposed on a skin patch can receive an induced voltage. In some embodiments, the current can be induced in the first electrode and an induced voltage can be received by the second electrode. Whether the second electrode is disposed in the blood pool or in contact with cardiac tissue can affect a magnitude of the induced voltage. Likewise, the current can be induced in the second electrode and an induced voltage can be received by the first electrode. Whether the first electrode is disposed in the blood pool or in contact with cardiac tissue can affect a magnitude of the induced voltage. In some embodiments, a current can be induced in another electrode disposed on the medical device and an induced voltage can be received by one or both of the first and second electrodes. Induced voltages associated with electrical signals received from the first and second electrodes can vary depending on whether one or more of the first and second electrodes are disposed in the blood pool or disposed against cardiac tissue, as discussed herein.

Some embodiments of the present disclosure can include a method for determining a cardiac activation associated with endocardial tissue, according to various embodiments of the present disclosure. As discussed, the method can include receiving a first electrical signal from a first electrode disposed on a first side of a tip portion of a medical device. In some embodiments, the method can include receiving a second electrical signal from a second electrode disposed on a second side of the tip portion of the medical device. As previously discussed, the first electrode and the second electrode can be disposed vertically adjacent with respect to one another in a manner analogous to that depicted and discussed herein.

In some embodiments, the method can include determining a characteristic associated with the cardiac activation, wherein the cardiac activation is in a direction that is normal to a surface of the endocardial tissue. In an example, because the first electrode and the second electrode are vertically adjacent to one another, as a cardiac activation travels through endocardial tissue, an electrical activation signal can be received by the first electrode disposed against the tissue and can then be received by the second electrode that is vertically adjacent to the first electrode. For instance, as the electrical activation signal travels toward a surface of the endocardial tissue on which the first electrode is disposed, the electrical activation signal can travel in a direction that is normal to the surface of the endocardial tissue, toward the first electrode. As the electrical activation signal reaches the surface of the endocardial tissue on which the first electrode is disposed, a first electrical signal can be received from the first electrode. The electrical activation signal can then travel through a portion of the blood pool and can be received by the second electrode disposed vertically adjacent to the first electrode. This can allow for a better measurement of the electrical activation signal since the two electrodes are disposed vertically adjacent to one another.

In some embodiments, the characteristic associated with the cardiac activation can include a direction of the cardiac activation. For example, a determination that a component of a directional vector of the cardiac activation is normal to a surface of the endocardial tissue can be made. In some embodiments, it can be common for cardiac activation to be in a direction that is normal to the surface of the endocardial tissue. For example, in thick ventricular tissue, cardiac activation can be in a direction that is normal to the surface of the endocardial tissue.

In some embodiments, the method can include filtering out noise from the first electrical signal based on the second electrical signal. For example, where the first electrode is disposed against the surface of the endocardial tissue, surrounding noise can have negative effects on the first electrical signal associated with the first electrode. The surrounding noise can be caused by stray electrical signals that are flowing through the blood pool in some embodiments. Accordingly, the second electrode, which is disposed in the blood pool can receive any stray electrical signals that are flowing through the blood pool, which can be represented in the second electrical signal associated with the second electrode. In some embodiments, the second electrical signal can be used to filter out the stray electrical signals from the first electrical signal. In some embodiments, the methods discussed herein can be executed by a computer such as that discussed in relation to FIG. 5.

Figure 6:
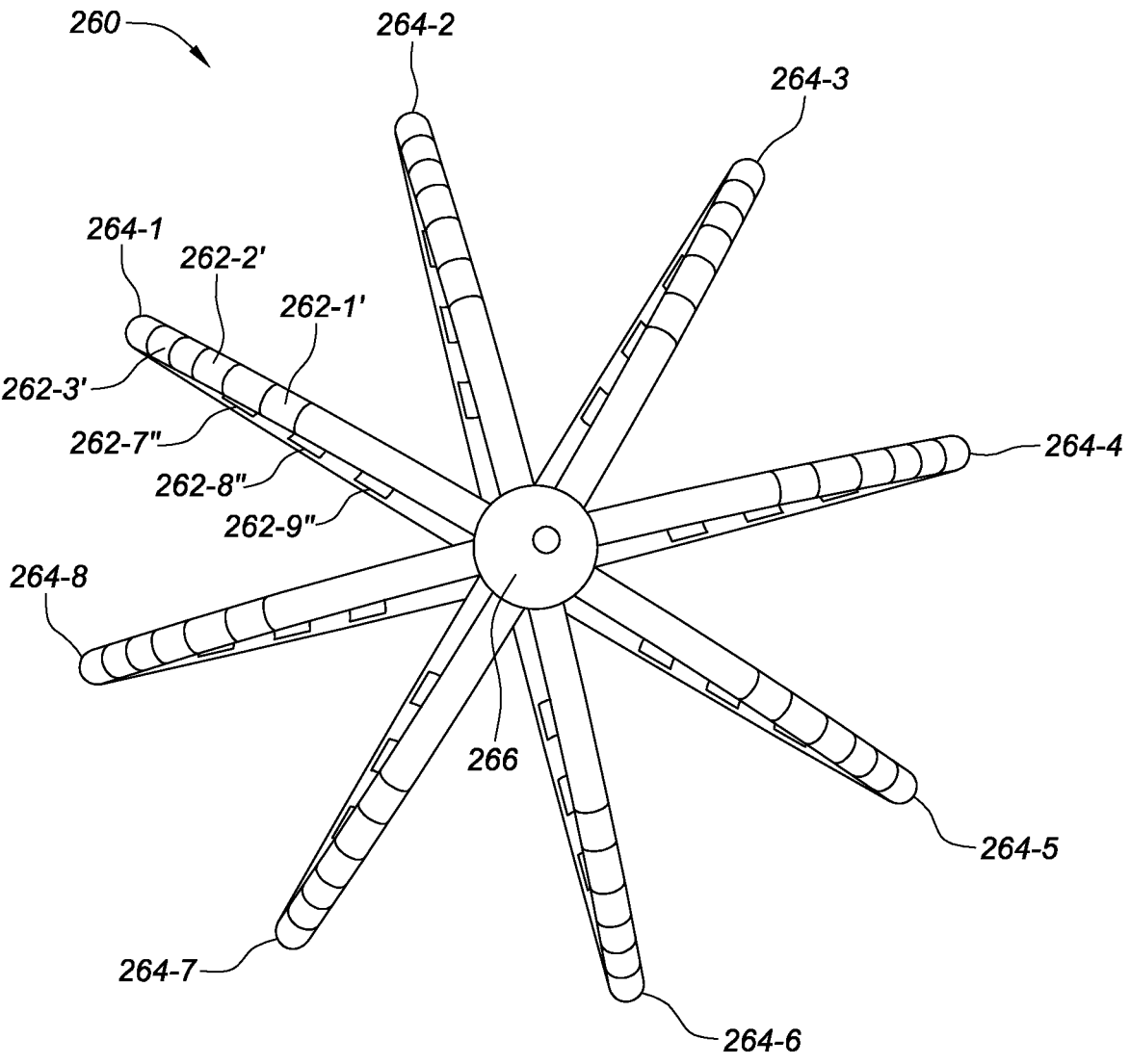
FIG. 6 is a top view of an electrode basket catheter, which includes a plurality of curved electrodes disposed on a plurality of splines of the basket catheter, in accordance with embodiments of the present disclosure.

FIG. 6 is a top view of an electrode basket catheter 260, which includes a plurality of curved electrodes 262-1', 262-2', 262-3', 262-7", 262-8", 262-9" disposed on a plurality of splines (e.g., spline 264-1) of the basket catheter 260, in accordance with embodiments of the present disclosure. As depicted, the electrode basket catheter 260 can include a plurality of splines 264-1, 264-2, . . . , 264-8 on which the plurality of curved electrodes 262-1', 262-2', 262-3', 262-7", 262-8", 262-9" are disposed. The electrode basket catheter 260 is illustrated in an expanded configuration. For example, the electrode basket catheter 260 can include a flexible framework that is formed by the plurality of splines 264-1, 264-2, . . . , 264-8, hereinafter referred to in the plural as splines 264, which can be connected at their proximal ends via a proximal connector (not depicted) and can be connected at their distal ends via a distal connector 266. The proximal connector can be moved in a proximal direction away from the distal connector 266 to collapse the splines 264 and can be moved in a distal direction toward the distal connector 266 to expand the splines 264 into the expanded state, which is depicted. A plurality of electrodes 262-1', 262-2', 262-3', 262-7", 262-8", 262-9" can be disposed on each one of the splines 264. For ease of illustration, only the electrodes 262-1', 262-2', 262-3', 262-7", 262-8", 262-9" disposed on a first spline 264-1 are depicted.

In some embodiments, outer curved electrodes 262-1', 262-2', 262-3' can be disposed on an outer face of one or more of the splines 264 and inner curved electrodes 262-7", 262-8", 262-9" can be disposed on an inner face of one or more of the splines 264. For example, a cross-section of each one of the splines 264 can be similar to or the same as the cross-sections of the arms depicted and discussed in relation to FIGS. 1D to 2C. In some embodiments, as depicted, the outer curved electrodes 262-1', 262-2', 262-3' can have a greater circumferential width than the inner curved electrodes 262-7", 262-8", 262-9". In some embodiments, the outer curved electrodes 262-1', 262-2', 262-3' can have a circumferential width that is less than the inner curved electrodes 262-7", 262-8", 262-9". In some embodiments, the outer curved electrodes 262-1', 262-2', 262-3' can have a circumferential width that is approximately equal to the inner curved electrodes 262-7", 262-8", 262-9". Furthermore, the basket catheter 260 can include those features as discussed in relation to FIGS. 1A to 5.

Figures 7A, 7B:
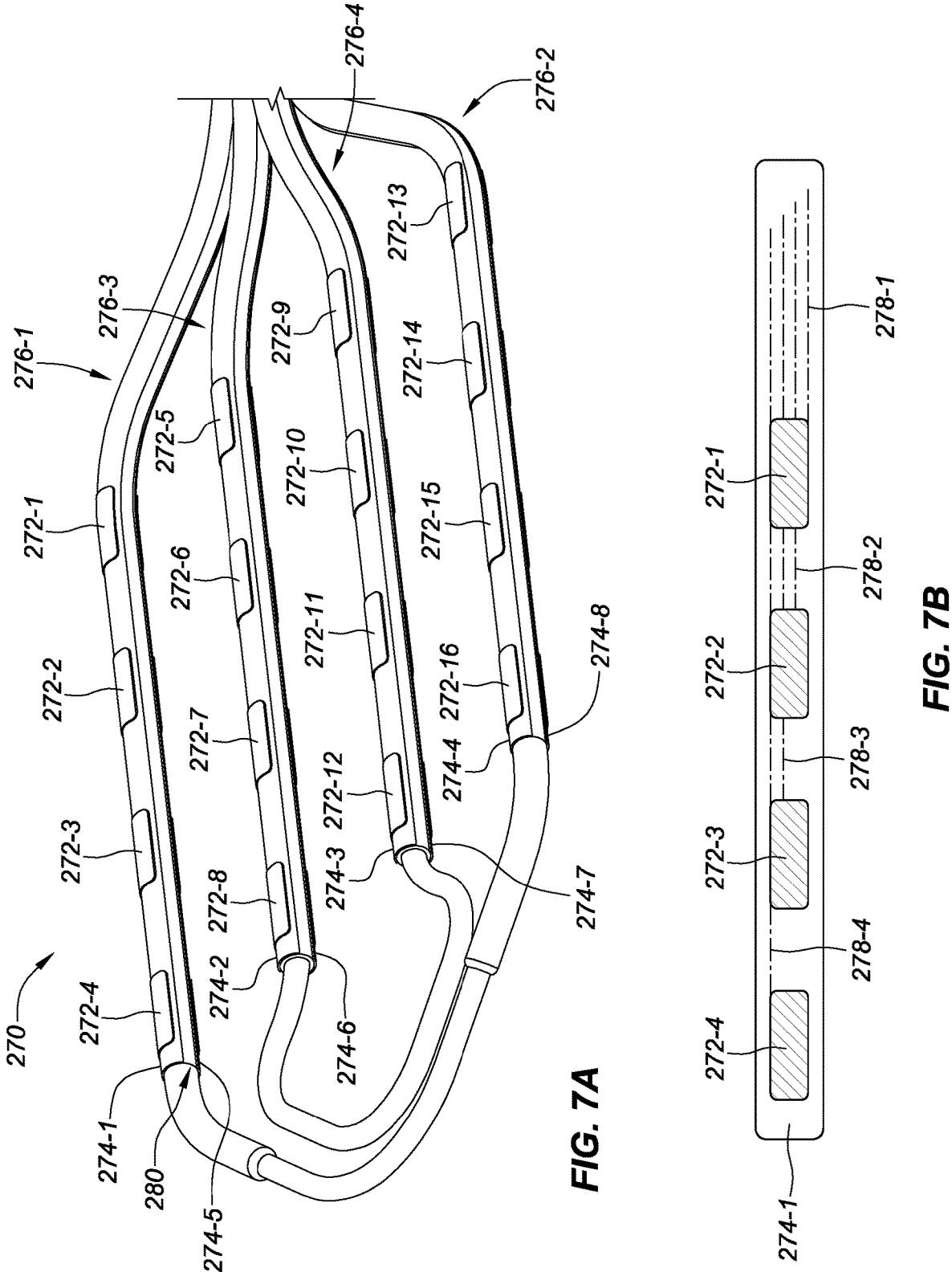
FIG. 7A depicts an isometric side and top view of a high density electrode mapping catheter that includes curved electrodes disposed on flexible circuits, according to various embodiments of the present disclosure.
FIG. 7B is a schematic representation of a flexible circuit, as depicted in FIG. 7A, in accordance with embodiments of the present disclosure.

FIG. 7A depicts an isometric side and top view of a high density electrode mapping catheter 270 that includes curved electrodes 272-1, 272-2, . . . , 274-16 (e.g., microelectrodes) disposed on flexible circuits 274-1, 274-2, 274-3, 274-4, according to various embodiments of the present disclosure. Hereinafter, the curved electrodes 272-1, 272-2, . . . , 272-16 are collectively referred to in the plural as curved electrodes 272. In some embodiments, the curved electrodes 272 and flexible circuits 274-1, 274-2, 274-3, 274-4 can be disposed on the top of the flexible portion of the high density electrode mapping catheter 270 and on a bottom portion, although the curved electrodes 272 and flexible circuits 274-5, 274-6, 274-7, 274-8 disposed on the bottom portion are hidden or partially hidden from view in FIG. 7A. In an example, the flexible circuits 274-1, 274-2, 274-3, 274-4 can be disposed on a top half of the flexible portion of the high density electrode mapping catheter 270 and the flexible circuits 274-5, 274-6, 274-7, 274-8 can be disposed on a bottom half of the flexible portion of the high density electrode mapping catheter 270. In some embodiments, the high density electrode mapping catheter 270 can include curved electrodes 272, as previously discussed herein. For example, the curved electrodes 272 can be curved about respective arm longitudinal axes, as discussed in relation to FIG. 1B. However, in some embodiments, the high density electrode mapping catheter 270 can include electrodes that are not curved.

In some embodiments, the high density electrode mapping catheter 270 can include one or more flexible circuits disposed on each one of the first outboard arm 276-1, second outboard arm 276-2, first inboard arm 276-3, and second inboard arm 276-4. In some embodiments, a first flexible circuit 274-1 can be disposed on the first outboard arm 276-1, a second flexible circuit 274-2 can be disposed on the first inboard arm 276-3, a third flexible circuit 274-3 can be disposed on the second inboard arm 276-4, and a fourth flexible circuit 274-4 can be disposed on the second outboard arm 276-2. The flexible circuits 274-1, 274-2, 274-3, 274-4 can be disposed directly on each one of the arms 276-1, 276-2, 276-3, 276-4. In some embodiments, the flexible circuits 274-1, 274-2, 274-3, 274-4 can be attached directly to each one of the arms 276-1, 276-2, 276-3, 276-4 via an adhesive bonding agent. The flexible circuits 274-1, 274-2, 274-3, 274-4 can extend proximally along a flexible tip portion of the high density electrode mapping catheter 270 and can terminate at or near a junction of the flexible tip portion. In some embodiments, individual leads can be connected to conductive traces included in the flexible circuits 274-1, 274-2, 274-3, 274-4, as further discussed herein.

In some embodiments, each one of the flexible circuits 274-1, 274-2, 274-3, 274-4 can be constructed through deposition of various materials directly on each one of the arms 276-1, 276-2, 276-3, 276-4, as further discussed in U.S. patent application Ser. No. 15/331,562, which is hereby incorporated by reference as though fully set forth herein. For example, in some embodiments, a dielectric layer can be formed directly on each one of the arms 276-1, 276-2, 276-3, 276-4. One or more curved electrodes 272 can be formed on top of the dielectric layer, along with leads to each respective curved electrode 272. FIG. 7B is a schematic representation of the first flexible circuit 274-1, as depicted in FIG. 7A, in accordance with embodiments of the present disclosure. For ease of illustration, the proximal end of the first flexible circuit 274-1 is not shown. In some embodiments, the flexible circuit 274-1 can include an insulative outer layer through which, or on which, the curved electrodes 272-1, 272-2, 272-3, 272-4 are disposed. In some embodiments, the flexible circuit 274-1 can include an insulative inner layer that insulates the flexible circuit 274-1 from a respective one of the arms (e.g., a metal understructure of the arm).

The curved electrodes 272-1, 272-2, 272-3, 272-4 can include features such as those previously disclosed herein.

In some embodiments, the flexible circuit 274-1 can include a conductive trace (e.g., lead) that is electrically coupled with each one of the curved electrodes 272-1, 272-2, 272-3, 272-4. For example, a first electrical trace 278-1 can be electrically coupled with the first curved electrode 272-1, a second electrical trace 278-2 can be electrically coupled with the second curved electrode 272-2, a third electrical trace 278-3 can be electrically coupled with the third curved electrode 272-3, and a fourth electrical trace 278-4 can be electrically coupled with the fourth curved electrode 272-4. Each one of the electrical traces 278-1, 278-2, 278-3, 278-4 can extend proximally along the flexible circuit 274-1 and can terminate at a junction. In some embodiments, the junction can be located on the high density electrode mapping catheter 270, along a shaft (not depicted) of the high density electrode mapping catheter 270, or some other area located proximally with respect to the shaft of the high density electrode mapping catheter, such as at a main control 232, as depicted in FIG. 5. The one or more electrical traces 278-1, 278-2, 278-3, 278-4 can transmit one or more signals from each one of the curved electrodes 272. In some embodiments, one or more signals can be transmitted to one or more of the curved electrodes 272 to perform a therapeutic action (e.g., ablation) and/or diagnostic action. As depicted, the electrical traces 278-1, 278-2, 278-3, 278-4 are depicted in phantom, since they are disposed under an insulative and/or dielectric layer. In some embodiments, one or more vias can be formed in the insulative and/or dielectric layer between the electrical traces 278-1, 278-2, 278-3, 278-4 and each one of the respective curved electrodes 272. Thus, in an example, with respect to the first curved electrode 272-1, second electrical trace 278-2, third electrical trace 278-3, and fourth electrical trace 278-4 can pass underneath the first curved electrode 272-1 and are not electrically coupled with the first curved electrode 272-1.

As further depicted in FIG. 7A, a flexible circuit can be disposed on both sides of the high density electrode mapping catheter 270. For example, a fifth, sixth, seventh, and eighth flexible circuit 274-5, 274-6, 274-7, 274-8 are disposed on the bottom of the high density electrode mapping catheter 270. In some embodiments, a same pattern of curved electrodes can be disposed on the bottom of the high density electrode mapping catheter 270. As depicted, a gap 280 can exist between a top flexible circuit 274-1 and a bottom flexible circuit 274-5, such that the top flexible circuit 274-1 does not overlap the bottom flexible circuit 274-5.

In some embodiments, the flexible circuit 274-1 on which the curved electrodes are disposed can be formed from a flexible material, as previously mentioned. Accordingly, the flexible circuit 274-1 can be applied to a respective one of the arms (e.g., first outboard arm 276-1). In some embodiments, the flexible circuit 274-1 can envelop a portion of the respective one of the arms. For example, the flexible circuit 274-1 can envelop a top portion of the first outboard arm 276-1. In some embodiments, an additional flexible circuit 274-5 can envelop a bottom portion of the first outboard arm 276-1, leaving a gap 280 between the two flexible circuits that run longitudinally along the first outboard arm 276-1. However, in some embodiments, the pair of flexible circuits 274-1, 274-5 can overlap one another and/or a single flexible circuit can be wrapped about a respective one of the arms. For example, a single flexible circuit that includes two rows of curved electrodes can be wrapped about a respective one of the arms such that a first row of curved electrodes is disposed on a top of the respective one of the arms and the second row of curved electrodes is disposed on a bottom of the respective one of the electrodes.

In some embodiments, the curved electrodes 272 can be flexible, such that the curved electrodes 272 can flex along with the flex circuit. However, in some embodiments, the curved electrodes 272 can be preformed to a curvature of the arms 276-1, 276-2, 276-3, 276-4 of the high density electrode mapping catheter 270.

In some embodiments, the flex circuits 274-1, 274-2, 274-3, 274-4 can be disposed directly on an understructure that forms each one of the arms 276-1, 276-2, 276-3, 276-4, which can consist of a flexible metal, such as Nitinol. However, in some embodiments, the understructure can be inserted in a tubing. The tubing can be a heat shrink tubing, in some embodiments, which can be heated, thus shrinking the tubing around each one of the arms 276-1, 276-2, 276-3, 276-4. The flex circuits 274 can then be applied to an exterior of the heat shrink tubing. In some embodiments, the arms 276-1, 276-2, 276-3, 276-4 can be coated with a material (e.g., polymer), which can be flexible, and the flex circuits 274 can be applied to the exterior of the coating material. In some embodiments, the tubing through which the understructure is inserted and/or the material that coats the understructure can include a polymer, such as PEBAX®. In some embodiments, the understructure of the high density electrode mapping catheter 270 can be inserted through a tube that does not include a flexible circuit, as further depicted and described in relation to FIGS. 8 and 9.

Figures 8, 9:
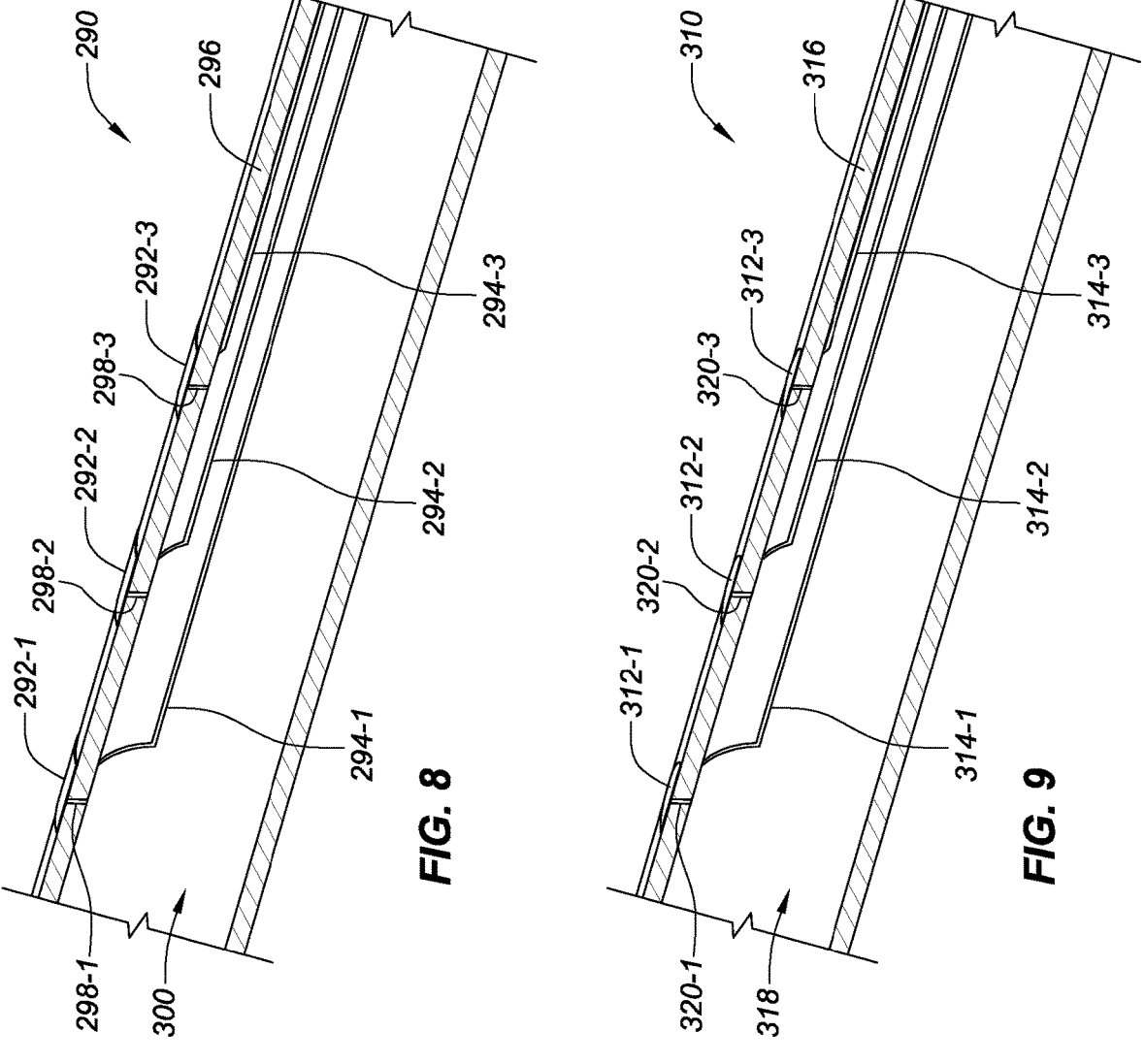
FIG. 8 depicts a reflowed tube that includes electrodes and conductive traces electrically coupled with the electrodes, in accordance with embodiments of the present disclosure.
FIG. 9 depicts an electrode tube that includes electrodes and conductive wires electrically coupled to the electrodes, in accordance with embodiments of the present disclosure.

FIG. 8 depicts a reflowed electrode tube 290 that includes electrodes 292-1, 292-2, 292-3 and conductive traces 294-1, 294-2, 294-3 electrically coupled with the electrodes 292-1, 292-2, 292-3 (e.g., microelectrodes), in accordance with embodiments of the present disclosure. The reflowed electrode tube 290 can include sidewall 296, in which the electrodes 292-1, 292-2, 292-3 and/or the conductive traces 294-1, 294-2, 294-3 are disposed. In some embodiments, the conductive traces 294-1, 294-2, 294-3 can extend along an inner surface of the sidewall 296 and/or within the sidewall 296. In some embodiments, vias 298-1, 298-2, 298-3 can be formed in the sidewall, such that a passage is created between a lumen 300 defined by the reflowed electrode tube 290 and an outer surface of the reflowed electrode tube 290. Although electrodes 292-1, 292-2, 292-3 are depicted as being disposed on one side of the reflowed electrode tube 290, electrodes can also be disposed on an opposite side of the reflowed electrode tube 290 to form corresponding pairs of electrodes 292-1, 292-2, 292-3.

The conductive traces 294-1, 294-2, 294-3 can extend distally from a proximal end of the reflowed electrode tube 290 and can terminate at respective ones of the electrodes 292-1, 292-2, 292-3. For example, the conductive traces 294-1, 294-2, 294-3 can extend distally from a proximal end of the reflowed electrode tube 290 and can extend through each one of the respective vias 298-1, 298-2, 298-3 and can be coupled to each one of the respective electrodes 292-1, 292-2, 292-3. The one or more conductive traces 294-1, 294-2, 294-3 can transmit one or more signals from each one of the electrodes 292-1, 292-2, 292-3. In some embodiments, one or more signals can be transmitted to one or more of the electrodes 292-1, 292-2, 292-3 to perform a therapeutic action (e.g., ablation) and/or diagnostic action. In some embodiments, the electrodes 292-1, 292-2, 292-3 can be curved electrodes, as previously discussed herein. However, in some embodiments, the electrodes 292-1, 292-2, 292-3 can be flat electrodes.

In some embodiments, the reflowed electrode tube 290 can be reflowed around the electrodes 292-1, 292-2, 292-3 and conductive traces 294-1, 294-2, 294-3. For example, the electrodes 292-1, 292-2, 292-3 can be placed on the outer surface of the sidewall 296 and the conductive traces 294-1, 294-2, 294-3 can be placed on an inner surface of the sidewall 296 and threaded through each respective via 298-1, 298-2, 298-3. The tube can then be heated to reflow the tube and adhere the electrodes 292-1, 292-2, 292-3 to the outer surface of the sidewall 296 and adhere their respective conductive traces 294-1, 294-2, 294-3 to the inner surface of the sidewall 296.

In some embodiments, the electrodes 292-1, 292-2, 292-3 can be formed and/or disposed on a first surface of a flat polymer material and the conductive traces 294-1, 294-2, 294-3 can be formed and/or disposed on a second surface of the flat polymer that is opposite of the first surface. Interconnects can be formed between the first surface and the second surface of the flat polymer before or after placement of the electrodes 292-1, 292-2, 292-3 and the conductive traces 294-1, 294-2, 294-3, which can electrically couple the electrodes 292-1, 292-2, 292-3 and the conductive traces 294-1, 294-2, 294-3.

In some embodiments, the electrode tube 290 can be formed through printing the electrodes 292-1, 292-2, 292-3 and the conductive traces 294-1, 294-2, 294-3, as well as the sidewall 296 of the tube on a form to create the electrode tube 290. For example, through use of a printer (e.g., aerosol/ink jet technologies), the electrodes 292-1, 292-2, 292-3 and the conductive traces 294-1, 294-2, 294-3, as well as the sidewall 296 can be printed onto a circular form to create a tubular component (e.g., the electrode tube).

In some embodiments, a protective layer can be formed over the inner surface of the sidewall 296 and the conductive traces 294-1, 294-2, 294-3. The protective layer can be an insulative layer that prevents the conductive traces 294-1, 294-2, 294-3 from contacting other conductive material, such as an understructure of a flexible tip portion of a high density electrode mapping catheter 270, such as that depicted in relation to FIG. 7A.

In some embodiments, the reflowed electrode tube 290 with the electrodes 292-1, 292-2, 292-3 and conductive traces 294-1, 294-2, 294-3 can be disposed over the understructure of the flexible tip portion of a high density electrode mapping catheter 270. In an example, the reflowed electrode tube 290 can be disposed over a flexible understructure (e.g., formed from nitinol) of the flexible tip portion of the high density electrode mapping catheter 270. For instance, the reflowed electrode tube 290 can be coaxial with a respective arm of the understructure forming the flexible tip portion of the high density electrode mapping catheter 270.

The reflowed electrode tube 290 can be formed from a flexible material, such as a polymer (e.g., PEBAX®), which can allow the reflowed electrode tube 290 to flex with the flexible understructure. In some embodiments, the reflowed electrode tube 290 can be adhered to the flexible understructure. For example, the reflowed electrode tube 290 can be adhered to the flexible understructure via an adhesive in some embodiments. In some embodiments, the reflowed electrode tube 290 can be frictionally fit to the flexible understructure. In some embodiments, the reflowed electrode tube 290 can be a heat shrink tube and can be adhered to the flexible understructure through application of heat to the reflowed electrode tube 290, causing the reflowed electrode tube 290 to shrink.

FIG. 9 depicts an electrode tube 310 that includes electrodes 312-1, 312-2, 312-3 (e.g., microelectrodes) and conductive wires 314-1, 314-2, 314-3 electrically coupled to the electrodes 312-1, 312-2, 312-3, in accordance with embodiments of the present disclosure. The electrode tube 310 can include sidewall 316 that defines a lumen 318. In some embodiments, the conductive wires 314-1, 314-2, 314-3 can extend through the lumen 318. In some embodiments, vias 320-1, 320-2, 320-3 can be formed in the sidewall, such that a passage is created between a lumen 318 defined by the electrode tube 310 and an outer surface of the electrode tube 310. Although electrodes 312-1, 312-2, 312-3 are depicted as being disposed on one side of the electrode tube 310, electrodes can also be disposed on an opposite side of the reflowed electrode tube 310 to form corresponding pairs of electrodes 312-1, 312-2, 312-3.

The conductive wires 314-1, 314-2, 314-3 can extend distally from a proximal end of the electrode tube 310 and can terminate at respective ones of the electrodes 312-1, 312-2, 312-3. For example, the conductive wires 314-1, 314-2, 314-3 can extend distally from a proximal end of the electrode tube 310 and can extend through each one of the respective vias 320-1, 320-2, 320-3 and can be coupled to each one of the respective electrodes 312-1, 312-2, 312-3. In some embodiments. The one or more conductive wires 314-1, 314-2, 314-3 can transmit one or more signals from each one of the electrodes 312-1, 312-2, 312-3. In some embodiments, one or more signals can be transmitted to one or more of the electrodes 312-1, 312-2, 312-3 to perform a therapeutic action (e.g., ablation) and/or diagnostic action. In some embodiments, the electrodes 312-1, 312-2, 312-3 can be curved electrodes, as previously discussed herein. However, in some embodiments, the electrodes 312-1, 312-2, 312-3 can be flat electrodes. In some embodiments, the electrodes can be spot electrodes.

In some embodiments, the electrodes 312-1, 312-2, 312-3 can be formed from a conductive epoxy. In an example, the conductive epoxy can include a silver filled one or two part epoxy. However, the epoxy could also be filled with another conductive materials, such as nickel and/or graphite, among other conductive material options. In an example, the conductive wires 314-1, 314-2, 314-3 can be threaded through the vias 320-1, 320-2, 320-3 and/or connected to a conductive plug disposed in each one of the vias 320-1, 320-2, 320-3. The conductive epoxy can then be deposited over the vias 320-1, 320-2, 320-3, such that the conductive epoxy is electrically coupled with the conductive wires 314-1, 314-2, 314-3 disposed in the vias and/or the conductive epoxy is electrically coupled with the conductive wires 314-1, 314-2, 314-3 via the conductive plugs disposed in the vias 320-1, 320-2, 320-3. In some embodiments, the conductive epoxy in its uncured state can be formed in particular shapes (e.g., circle, square, rectangle, triangle, etc.). Upon cure of the conductive epoxy, the conductive electrodes 312-1, 312-2, 312-3 can be formed.

In some embodiments, a protective sleeve can be formed over the inner surface of the sidewall 316 and can sandwich the conductive wires 314-1, 314-2, 314-3 between the protective sleeve and an inner wall of the sidewall 316. The protective sleeve can be an insulative layer that prevents the conductive wires 314-1, 314-2, 314-3 from contacting other conductive material and/or prevents an insulative coating (e.g., insulation) disposed around each one of the conductive wires from being worn.

In some embodiments, the electrode tube 310 with the electrodes 312-1, 312-2, 312-3 and conductive wires 314-1, 314-2, 314-3 can be disposed over the understructure of the flexible tip portion of a high density electrode mapping catheter 270, such as that depicted and disclosed in FIG. 7A. In an example, the electrode tube 310 can be disposed over a flexible understructure (e.g., formed from nitinol) of the flexible tip portion of the high density electrode mapping catheter 270. For instance, the electrode tube 310 can be coaxial with a respective arm of the understructure forming the flexible tip portion of the high density electrode mapping catheter 270.

The electrode tube 310 can be formed from a flexible material, such as a polymer (e.g., PEBAX®), which can allow the electrode tube 310 to flex with the flexible understructure. In some embodiments, the electrode tube 310 can be adhered to the flexible understructure. For example, the electrode tube 310 can be adhered to the flexible understructure via an adhesive in some embodiments. In some embodiments, the electrode tube 310 can be frictionally fit to the flexible understructure. In some embodiments, the electrode tube 310 can be a heat shrink tube and can adhered to the flexible understructure through application of heat to the electrode tube 310, causing the electrode tube 310 to shrink.

Although embodiments of the present disclosure are generally depicted in relation to a catheter with an inboard and outboard understructure and/or in relation to a basket catheter, embodiments of the present disclosure can be applied to any type of catheter. For example, embodiments of the present disclosure can be applied to any type of therapeutic and/or diagnostic catheter.

The embodiments of FIGS. 8 and 9 are discussed in relation to electrode tubes 290, 310, and electrodes 292-1, 292-2, 292-3, 312-1, 312-2, 312-3 disposed at their distal ends. However, embodiments of the present disclosure can further include an electrical connection hub disposed at a proximal end of the electrode tubes 290, 310. For example, a similar configuration as that depicted and discussed in FIGS. 8 and 9 can be employed at a proximal end of the electrode tubes 290, 310, with the exception that instead of electrodes 292-1, 292-2, 292-3, 312-1, 312-2, 312-3 being coupled to the proximal ends of the conductive wires 294-1, 294-2, 294-3, 314-1, 314-2, 314-3, electrical connection contacts are electrically coupled with the conductive wires to allow for the electrical coupling of the electrodes to, for example, a main control 232, as depicted in FIG. 5.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a high density electrode mapping catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A medical device, comprising:
a catheter shaft comprising a proximal end and a distal end, the catheter shaft defining a catheter shaft longitudinal axis;
a flexible tip portion located adjacent to the distal end of the catheter shaft, the flexible tip portion comprising a planar array comprising a first inboard arm, a second inboard arm, a first outboard arm, and a second outboard arm, each arm having a top face and a bottom face; and a plurality of curved electrode pairs disposed on each of the first inboard arm, the second inboard arm, the first outboard arm, and the second outboard arm, the plurality of curved electrode pairs forming a flexible array of curved electrodes adapted to conform to tissue, wherein each pair of the plurality of the curved electrode pairs includes a top curved electrode disposed on the top face of the respective arm and a bottom curved electrode disposed on the bottom face of the same respective arm, wherein each curved electrode of the plurality of curved electrode pairs does not extend around an entire circumference of each of the first inboard arm, the second inboard arm, the first outboard arm, and the second outboard arm, wherein selected ones of the plurality of curved electrode pairs are configured to be deactivated to form a pattern of a plurality of activated curved electrode pairs, the plurality of activated curved electrode pairs being configured to measure electrical signals produced by the tissue of a patient and provide ablation therapy to the tissue, wherein the plurality of curved electrode pairs disposed on one of the first inboard arm, the second inboard arm, the first outboard arm, and the second outboard arm are longitudinally staggered from the plurality of curved electrode pairs disposed on an adjacent one of the first inboard arm, the second inboard arm, the first outboard arm, and the second outboard arm to form an alternating arrangement, wherein, for each pair of the plurality of the curved electrode pairs, a first circumferential width of the top curved electrode is less than a second circumferential width of the bottom curved electrode such that a circumferential gap between edges of the top curved electrode and edges of the bottom curved electrode is between 20 degrees and 60 degrees.

2. The medical device of claim 1, wherein:

each of the first inboard arm, second inboard arm, first outboard arm, and second outboard arm extends along a respective arm longitudinal axis.

3. The medical device of claim 2, wherein:

a pair of flexible circuits is disposed on each one of the first inboard arm, second inboard arm, first outboard arm, and second outboard arm; and the plurality of curved electrode pairs are disposed on each one of the flexible circuits.

4. The medical device of claim 3, wherein a first flexible circuit of the pair of flexible circuits is disposed on the top face of each one of the arms and a second flexible circuit of the pair of flexible circuits is disposed on the bottom face of each one of the arms.

5. The medical device of claim 4, wherein a gap is defined between the first flexible circuit and the second flexible circuit that runs longitudinally along each one of the arms.

6. The medical device of claim 3, wherein each of the flexible circuits of each of the pair of flexible circuits includes electrical traces electrically coupled to each one of the plurality of curved electrode pairs.

7. The medical device of claim 1, wherein, for each of the plurality of curved electrodes pairs, the top curved electrode and the bottom curved electrode circumferentially extend about the respective arm such that an angle defined between a central axis of the respective arm and adjacent edges of the top curved electrode and the bottom curved electrode is in a range between 20 and 135 degrees.

8. The medical device of claim 1, further comprising a processor configured to electrically disconnect and deactivate the selected ones of the plurality of curved electrode pairs to form the pattern of the plurality of activated curved electrode pairs.

9. A catheter, comprising:

a catheter shaft comprising a proximal end and a distal end, the catheter shaft defining a catheter shaft longitudinal axis, wherein the shaft comprises one or more ring electrodes disposed along a length of the shaft for use in diagnostic, therapeutic, and/or mapping procedures;

a flexible tip portion located adjacent to the distal end of the catheter shaft, the flexible tip portion comprising a planar array comprising a first inboard arm, second inboard arm, first outboard arm, and second outboard arm, each arm having a top face and a bottom face; and a plurality of curved electrode pairs disposed on each of the first inboard arm, second inboard arm, first outboard arm, and second outboard arm, wherein each pair of the plurality of curved electrode pairs includes a top curved electrode on the top face of the respective arm and a bottom curved electrode on the bottom face of the same respective arm;

wherein the plurality of curved electrode pairs disposed on one of the first inboard arm, the second inboard arm, the first outboard arm, and the second outboard arm are longitudinally staggered from the plurality of curved electrode pairs disposed on an adjacent one of the first inboard arm, the second inboard arm, the first outboard arm, and the second outboard arm to form an alternating arrangement, wherein selected ones of the plurality of curved electrode pairs are configured to be deactivated to form a pattern of a plurality of activated curved electrode pairs, the plurality of activated curved electrode pairs being configured to measure electrical signals produced by a tissue of a patient and provide ablation therapy to the tissue, wherein, for each pair of the plurality of the curved electrode pairs, a first circumferential width of the top curved electrode is less than a second circumferential width of the bottom curved electrode such that a circumferential gap between edges of the top curved electrode and edges of the bottom curved electrode is between 20 degrees and 60 degrees.

* * * * *